(12) United States Patent
Moecks et al.

(10) Patent No.: US 7,700,299 B2
(45) Date of Patent: Apr. 20, 2010

(54) METHOD FOR PREDICTING THE RESPONSE TO A TREATMENT

(75) Inventors: Joachim Moecks, Mannheim (DE); Andreas Strauss, Penzberg (DE); Gerhard Zugmaier, Stuttgart (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 547 days.

(21) Appl. No.: 11/438,033

(22) Filed: May 19, 2006

(65) Prior Publication Data

US 2007/0037228 A1  Feb. 15, 2007

(30) Foreign Application Priority Data

Aug. 12, 2005  (EP) ................................. 05017663

(51) Int. Cl.
*G01N 33/53* (2006.01)
*G01N 33/48* (2006.01)
*G01N 33/566* (2006.01)
*G01N 33/567* (2006.01)

(52) U.S. Cl. .............................. 435/7.1; 435/4; 436/63; 436/64; 436/501; 436/503; 436/547; 436/548

(58) Field of Classification Search ..................... 435/6, 435/4, 7.1; 436/63, 64, 501, 503, 547, 548
See application file for complete search history.

(56) References Cited

U.S. PATENT DOCUMENTS

| 6,759,217 B2 * | 7/2004 | Kopreski .................... 435/91.2 |
| 2003/0225528 A1 | 12/2003 | Baker et al. |
| 2004/0013667 A1 | 1/2004 | Kelsey et al. |
| 2004/0106161 A1 | 6/2004 | Bossenmaier et al. |
| 2004/0157255 A1 | 8/2004 | Agus et al. |
| 2004/0248151 A1 | 12/2004 | Bacus et al. |

FOREIGN PATENT DOCUMENTS

| WO | WO 2004/005544 | 1/2004 |
| WO | WO 2004/091384 | 10/2004 |
| WO | WO 2005/011607 | 2/2005 |
| WO | WO 2005/047534 | 5/2005 |
| WO | WO 2005/049829 | 6/2005 |

OTHER PUBLICATIONS

Thogersen, V.B. et al, Cancer Research, 61: 6227-6233, 2001.*
Derynck, R., et al., Cell, vol. 38, pp. 287-297 (1984), XP000650165.
Coussens, L., et al., Science, vol. 230, No. 4730, pp. 1132-1139 (1985), XP009041156.
Shoyab, M., et al., Science, vol. 243, No. 4894, pp. 1074-1076 (1989), XP000574073.
Agus et al., Journal of Clin. Oncol., 23, pp. 2534-2543 (2005).
Altundag et al., Curr. Med. Chem.—Anti-Cancer Agents, 5, pp. 99-106 (2005).
Billings et al., Am. J. Pathol., 163, pp. 2451-2458 (2003).
Ciardiello et al., European Journal of Cancer, 39, pp. 1348-1354 (2003).
Hynes et al., Nature Reviews/ Cancer, 5, pp. 341-354 (2005).
Panico et al., Int. J. Cancer, 65, pp. 51-56 (1996).
Sridhar et al., Lance Oncology, 4, pp. 397-406 (2003).
European Journal of Cancer, Pergamon Press, Oxford, GB, vol. 38, Nov. 2002, p. S149, XP004403941; ISSN:0959-8049.
Willems et al., Anticancer Research, 25, pp. 1483-1489 (2005).
Köstler et al., Clinical Cancer Research, 10, pp. 1618-1624 (2004).
Menard et al., Oncogene, 44, pp. 6570-6578 (2003).
Bell, G.I., et al., Nucleic Acids Research, vol. 14, No. 21, pp. 8427-8446 (1986).

* cited by examiner

*Primary Examiner*—Alana M. Harris
*Assistant Examiner*—Anne L Holleran
(74) *Attorney, Agent, or Firm*—George W. Johnston; Patricia S. Rocha-Tramaloni; Gene J. Yao

(57) ABSTRACT

The invention is related to a method of predicting the response to a treatment with a HER inhibitor in a patient comprising the steps of assessing a biomarker or a combination of biomarkers selected from the group consisting of amphiregulin, an epidermal growth factor, a transforming growth factor alpha, and a HER2 biomarker in a biological sample from the patient and predicting the response to the treatment with the HER inhibitor in the patient by evaluating the results of the first step. Further uses and methods wherein these markers are used are disclosed.

11 Claims, 19 Drawing Sheets

Fig. 3

| Category | SERUM_TG F_ALPHA< 3.5 | SERUM_TG F_ALPHA> =3.5 | Total | |
|---|---|---|---|---|
| 0 | 14 | 14 | 28 | - fast progressive disease |
| 1 | 11 | 6 | 17 | - stable disease < 4 months |
| 2 | 2 | 1 | 3 | - stable disease 4 to 6 months |
| 3 | 3 | 0 | 3 | - stable disease >= 6 months |
| 4 | 2 | 0 | 2 | - partial response |
| Total | 32 | 21 | 53 | |

Fig. 4

| Category | SERUM_AM PHIREGUL IN<12 | SERUM_AM PHIREGUL IN>=12 | Total |
|---|---|---|---|
| 0 | 13 | 15 | 28 – fast progressive disease |
| 1 | 9 | 8 | 17 – stable disease < 4 months |
| 2 | 3 | 0 | 3 – stable disease 4 to 6 months |
| 3 | 3 | 0 | 3 – stable disease >= 6 months |
| 4 | 2 | 0 | 2 – partial response |
| Total | 30 | 23 | 53 |

Fig. 5

| Category | SERUM_EG F<150 | SERUM_EG F>=150 | Total | |
|---|---|---|---|---|
| 0 | 10 | 18 | 28 | - fast progressive disease |
| 1 | 8 | 9 | 17 | - stable disease < 4 months |
| 2 | 2 | 1 | 3 | - stable disease 4 to 6 months |
| 3 | 1 | 2 | 3 | - stable disease >= 6 months |
| 4 | 0 | 2 | 2 | - partial response |
| Total | 21 | 32 | 53 | |

Fig. 6

| Category | HER2P_EC D<18 | HER2P_EC D>=18 | Total | |
|---|---|---|---|---|
| 0 | 27 | 17 | 44 | - fast progressive disease |
| 1 | 20 | 4 | 24 | - stable disease < 4 months |
| 2 | 3 | 1 | 4 | - stable disease 4 to 6 months |
| 3 | 4 | 0 | 4 | - stable disease >= 6 months |
| 4 | 2 | 0 | 2 | - partial response |
| Total | 56 | 22 | 78 | |

Fig. 7

| Serum Marker | Exploratory marker cut off for group with greater benefit in TTP and/or TTD | Time to progression (TTP) | | Time to death (TTD) | |
|---|---|---|---|---|---|
| | | Number of events for TTP / N total | TTP P log-rank | Number of events for TTD / N total | P Log-rank TTD |
| TGF-alpha | < 3.5 pg/ml | 50/53 | 0.058 | 18/53 | 0.0002 |
| Amphiregulin | < 12 pg/ml | 50/53 | 0.030 | 18/53 | 0.29 |
| EGF | < 150 pg/ml | 50/53 | 0.85 | 18/53 | 0.046 |
| Her2-ECD | < 18 ng/ml | 74/78 | 0.014 | 30/78 | 0.0003 |

Fig. 16

| Category | HER2<18 and TGFA<2.4 | HER2>=18 or TGFA>=2.4 | Total |
|---|---|---|---|
| 0 | 7 | 29 | 36 - fast progressive disease |
| 1 | 8 | 10 | 18 - stable disease < 4 months |
| 2 | 1 | 3 | 4 - stable disease 4 to 6 months |
| 3 | 3 | 0 | 3 - stable disease >= 6 months |
| 4 | 2 | 0 | 2 - partial response |
| Total | 21 | 42 | 63 |

Fig. 17

| Serum Marker | Exploratory marker cut off for group with greater benefit in TTP and/or TTD | Time to progression (TTP) | | Time to death (TTD) | |
|---|---|---|---|---|---|
| | | Number of events for TTP / N total | TTP P log-rank | Number of events for TTD / N total | P Log-rank TTD |
| Her2-ECD/ TGF-alpha Combo score | < 18ng/ml HER2 ECD and/or < 2.4 pg/ml TGF-alpha | 60/63 | 0.0014 | 25/63 | 0.0014 |

US 7,700,299 B2

METHOD FOR PREDICTING THE RESPONSE TO A TREATMENT

PRIORITY TO RELATED APPLICATIONS

This application claims the benefit of European Application No. 05017663.5, filed Aug. 12, 2005, which is hereby incorporated by reference in its entirety.

FIELD OF THE INVENTION

The invention is related to a method of predicting the response to a treatment with a HER inhibitor, preferably a HER dimerization inhibitor, in a patient comprising the steps of assessing a marker gene or a combination of marker genes selected from the group consisting of an epidermal growth factor, a transforming growth factor alpha and a HER2 marker gene or a combination of marker genes comprising an amphiregulin marker gene and a marker gene selected from an epidermal growth factor, a transforming growth factor alpha and a HER2 marker gene in a biological sample from the patient and predicting the response to the treatment with the HER inhibitor in the patient by evaluating the results of the first step. Further uses and methods wherein these markers are used are disclosed.

BACKGROUND OF THE INVENTION

The human epidermal growth factor receptor (ErbB or HER) family comprises four members (HER1-4) that, through the activation of a complex signal cascade, are important mediators of cell growth, survival and differentiation. At least 11 different gene products from the epidermal growth factor (EGF) superfamily bind to three of these receptors, EGFR (also called ErbB1 or HER1), HER3 (ErbB3) and HER4 (ErbB4). Although no ligand has been identified that binds and activates HER2 (ErbB2 or neu), the prevailing understanding is that HER2 is a co-receptor that acts in concert with other HER receptors to amplify and in some cases initiate receptor-ligand signaling. Dimerization with the same receptor type (homodimerization) or another member of the HER family (heterodimerization) is essential for their activity. HER2 is the preferred dimerization partner for other HER family members. The role of the HER family in many epithelial tumor types is well documented and has led to the rational development of novel cancer agents directed specifically to HER receptors. The recombinant humanized anti-HER2 monoclonal antibody (MAb) trastuzumab is a standard of care in patients with HER2-positive metastatic breast cancer (MBC). Overexpression/amplification of the HER2 protein/gene, which occurs in 20-30% of breast cancer cases, is a prerequisite for treatment with trastuzumab.

Pertuzumab (Omnitarg™; formerly 2C4) is the first of a new class of agents known as HER dimerization inhibitors (HDIs). Pertuzumab binds to HER2 at its dimerization domain, thereby inhibiting its ability to form active dimer receptor complexes and thus blocking the downstream signal cascade that ultimately results in cell growth and division. Pertuzumab is a fully humanized recombinant monoclonal antibody directed against the extracellular domain of HER2. Binding of Pertuzumab to the HER2 on human epithelial cells prevents HER2 from forming complexes with other members of the HER family (including EGFR, HER3, HER4) and probably also HER2 homodimerization. By blocking complex formation, Pertuzumab prevents the growth-stimulatory effects and cell survival signals activated by ligands of HER1, HER3 and HER4 (e.g. EGF, TGFα, amphiregulin, and the heregulins). Other names for Pertuzumab are 2C4 or Pertuzumab. Pertuzumab is a fully humanized recombinant monoclonal antibody based on the human IgG1(κ) framework sequences. The structure of Pertuzumab consists of two heavy chains (449 residues) and two light chains (214 residues). Compared to Trastuzumab (Herceptin®), Pertuzumab has 12 amino acid differences in the light chain and 29 amino acid differences in the IgG1 heavy chain. WO 2004/092353 and WO 2004/091384 present investigations that the formation of heterodimers of HER2 with other receptors should be linked to the effectiveness or suitability of Pertuzumab.

Zabrecky, J. R. et al., J. Biol. Chem. 266 (1991) 1716-1720 disclose that the release of the extracellular domain of HER2 may have implications in oncogenesis and its detection could be useful as a cancer diagnostic. Colomer, R. et al., Clin. Cancer Res. 6 (2000) 2356-2362 disclose circulating HER2 extracellular domain and resistance to chemotherapy in advanced breast cancer. The prognostic and predictive values of the extracellular domain of HER2 is reviewed by Hait, W. N., Clin. Cancer Res. 7 (2001) 2601-2604.

SUMMARY OF THE INVENTION

There is still a need to provide further methods for determining the progression of disease in a cancer patient treated with a HER dimerization inhibitor.

Therefore, in an embodiment of the invention, a method of predicting the response to a treatment with a HER inhibitor, preferably a HER dimerization inhibitor, in a patient is provided comprising the steps of:
  (a) determining the expression level or amount of one or more biomarker in a biological sample from a patient wherein the biomarker or biomarkers are selected from the group consisting of:
    (1) transforming growth factor alpha;
    (2) HER2;
    (3) amphiregulin; and
    (4) epidermal growth factor;
  (b) determining whether the expression level or amount assessed in step (a) is above or below a certain quantity that is associated with an increased or decreased clinical benefit to a patient; and
  (c) predicting the response to the treatment with the HER inhibitor in the patient by evaluating the results of step (b).

In another embodiment of the invention, a probe that hybridizes with the polynucleotides of the above biomarkers under stringent conditions or an antibody that binds to the proteins of the above biomarkers is used for predicting the response to treatment with a HER inhibitor in a patient or used for selecting a composition for inhibiting the progression of disease in a patient.

In still another embodiment of the invention, a kit is provided comprising a probe that anneals with a biomarker polynucleotide under stringent conditions or an antibody that binds to the biomarker protein.

In still another embodiment of the invention, a method of selecting a composition for inhibiting the progression of disease in a patient is provided, the method comprising:
  (a) separately exposing aliquots of a biological sample from a cancer patient in the presence of a plurality of test compositions;
  (b) comparing the level of expression of one or more biomarkers selected from the group consisting of amphiregulin, epidermal growth factor, transforming growth factor alpha and HER2 in the aliquots of the biological sample contacted with the test compositions and the level of expression of such biomarkers in an aliquot of the biological sample not contacted with the test compositions; and (c) selecting one of the test compositions which alters the level of expression of a particular biomarker or biomarkers in the aliquot of the biological sample contacted with the test composition and the level of expression of the corresponding biomarker or biomarkers in the aliquot of the biological sample not contacted with the test composition is an indication for the selection of the test composition.

In yet another embodiment of the invention, a method of identifying a candidate agent is provided said method comprising:

(a) contacting an aliquot of a biological sample from a cancer patient with the candidate agent and determining the level of expression of one or more biomarkers selected from the group consisting of amphiregulin, epidermal growth factor, transforming growth factor alpha and HER2 in the aliquot;

(b) determining the level of expression of a corresponding biomarker or of a corresponding combination of biomarkers in an aliquot of the biological sample not contacted with the candidate agent;

(c) observing the effect of the candidate agent by comparing the level of expression of the biomarker or biomarkers in the aliquot of the biological sample contacted with the candidate agent and the level of expression of the corresponding biomarker or biomarkers in the aliquot of the biological sample not contacted with the candidate agent; and (d) identifying said agent from said observed effect, wherein an at least 10% difference between the level of expression of the biomarker or biomarkers in the aliquot of the biological sample contacted with the candidate agent and the level of expression of the corresponding biomarker or biomarkers in the aliquot of the biological sample not contacted with the candidate agent is an indication of an effect of the candidate agent.

In yet another embodiment, a candidate agent identified by the method according to the invention or a pharmaceutical preparation comprising an agent according to the invention is provided.

In yet another embodiment of the invention, an agent according to the invention is provided for the preparation of a composition for the treatment of cancer.

In still another embodiment of the invention, a method of producing a drug is provided comprising:

(i) synthesizing the candidate agent identified as described above or an analog or derivative thereof in an amount sufficient to provide said drug in a therapeutically effective amount to a subject; and/or (ii) combining the drug candidate or the candidate agent identified as described above or an analog or derivative thereof with a pharmaceutically acceptable carrier.

In yet another embodiment of the invention, a biomarker protein or a biomarker polynucleotide selected from the group consisting of an amphiregulin biomarker, and epidermal growth factor biomarker, a transforming growth factor alpha biomarker and a HER2 biomarker protein or polynucleotide is used for deriving a candidate agent or for selecting a composition for inhibiting the progression of a disease in a patient.

In another embodiment of the invention, a HER inhibitor, preferably a HER dimerization inhibitor, is used for the manufacture of a medicament for treating a human cancer patient characterized in that said treating or treatment includes assessing in a biological sample from the patient: one or more biomarkers selected from the group consisting of amphiregulin biomarker, epidermal growth factor biomarker, transforming growth factor alpha biomarker, and HER2 biomarker. In a particular embodiment, one or more biomarkers are assessed wherein the biomarkers are selected from the group consisting of epidermal growth factor, transforming growth factor alpha, and HER2. In another particular embodiment, a transforming growth factor alpha biomarker is assessed in combination with one or more biomarkers selected from the group consisting of epidermal growth factor, amphiregulin, and HER2. In another particular embodiment, a HER2 biomarker is assessed in combination with one or more biomarkers selected from the group consisting of epidermal growth factor, transforming growth factor alpha, and amphiregulin.

In another particular embodiment, a epidermal growth factor biomarker is assessed in combination with one or more biomarkers selected from the group consisting of amphiregulin, transforming growth factor alpha, and HER2.

In another particular embodiment, an amphiregulin biomarker is assessed in combination with one or more biomarkers selected from the group consisting of epidermal growth factor, transforming growth factor alpha, and HER2.

BRIEF DESCRIPTION OF THE FIGURES

FIG. 3: Ordinal clinical benefit TGF-alpha FIG. 4: Ordinal clinical benefit Amphiregulin FIG. 5: Ordinal clinical benefit EGF FIG. 6: Ordinal clinical benefit HER2-ECD FIG. 7: Overview exploratory cut-points and log-rank p-values for TTP and TTD for Amphiregulin, EGF, TGF-alpha, HER2-ECD FIG. 16: As example for a combination score, further improving the separation between the greater clinical benefit/lesser clinical benefit groups in TTP: Ordinal clinical benefit HER2-ECD TGF alpha combination FIG. 17: Overview exploratory cut-points and log-rank p-values for TTP and TTD for a combination of TGF-alpha and HER2-ECD

DETAILED DESCRIPTION OF THE INVENTION

Figure 1:
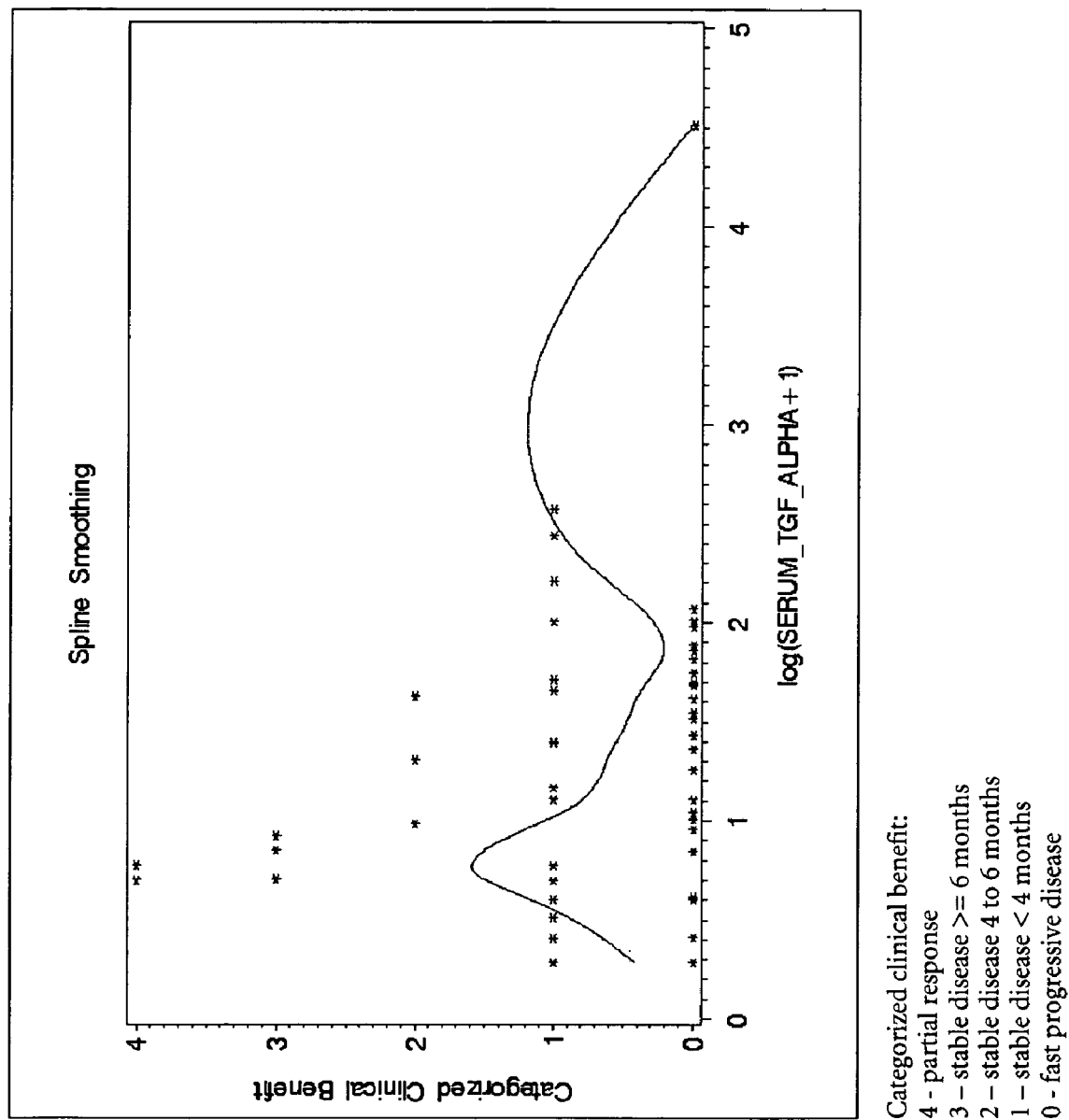
FIG. 1: Scatterplot TGF-alpha logarithmic transformation versus categorized clinical benefit

The articles "a" and "an" are used herein to refer to one or to more than one (i.e. to at least one) of the grammatical object of the article. By way of example, "an element" means one element or more than one element.

The term "biological sample" shall generally mean any biological sample obtained from an individual, body fluid, cell line, tissue culture, or other source. Body fluids are e.g. lymph, sera, plasma, urine, semen, synovial fluid and spinal fluid. Methods for obtaining tissue biopsies and body fluids from mammals are well known in the art. If the term "sample" is used alone, it shall still mean that the "sample" is a "biological sample", i.e. the terms are used interchangeably.

The term "response of a patient to treatment with a HER inhibitor" or "response of a patient to treatment with a HER dimerization inhibitor" refers to the clinical benefit imparted to a patient suffering from a disease or condition (such as cancer) from or as a result of the treatment with the HER inhibitor (e.g., a HER dimerization inhibitor). A clinical benefit includes a complete remission, a partial remission, a stable disease (without progression), progression-free survival, disease free survival, improvement in the time-to-progression (of the disease), improvement in the time-to-death, or improvement in the overall survival time of the patient from or as a result of the treatment with the HER dimerization inhibitor. There are criteria for determining a response to therapy and those criteria allow comparisons of the efficacy to alternative treatments (Slapak and Kufe, Principles of Cancer Therapy, in Harrisons's Principles of Internal Medicine, 13th edition, eds. Isselbacher et al., McGraw-Hill, Inc., 1994). For example, a complete response or complete remission of cancer is the disappearance of all detectable malignant disease. A partial response or partial remission of cancer may be, for example, an approximately 50 percent decrease in the product of the greatest perpendicular diameters of one or more lesions or where there is not an increase in the size of any lesion or the appearance of new lesions.

As used herein, the term "progression of cancer" includes and may refer to metastasis; a recurrence of cancer, or an at least approximately 25 percent increase in the product of the greatest perpendicular diameter of one lesion or the appearance of new lesions. The progression of cancer, preferably breast cancer, is "inhibited" if recurrence or metastasis of the cancer is reduced, slowed, delayed, or prevented.

As used herein, the term "Time To Progression/death" (also referred to as "TPP") or Progression-Free Survival (also referred to as "PFS") refers to a clinical endpoint frequently used in oncology trials (that includes but is not limited to clinical trials with reference to the present invention). The measurement for each patient equals the time elapsed from onset of the treatment of a patient in a trial (as defined in the protocol [i.e, see the examples infra]) until the detection of a malignancy progression (as defined in the protocol) or the occurrence of any fatality (whatever is first). If the observation of the patient was stopped (e.g. at study end) after a period and no event was observed, then this observation time t is called "censored."

As used herein, the term "Time To Death" (also referred to as "TTD") or "Overall Survival" (also referred to as "OS") refers to a clinical endpoint frequently used in oncology trials (that includes but is not limited to clinical trials with reference to the present invention). The measurement for each patient equals the time elapsed from onset of the treatment of a patient in a trial (as defined in the protocol [i.e., see the examples infra]) until the occurrence of any fatality. If the observation of the patient is stopped (e.g. at study end) after a period t and the patient survived to this time, then this observation time t is called "censored."

As used herein, the term "covariate" refers to certain variables or information relating to a patient. The clinical endpoints are frequently considered in regression models, where the endpoint represent the dependent variable and the biomarkers represent the main or target independent variables (regressors). If additional variables from the clinical data pool are considered these are denoted as (clinical) covariates. The term "clinical covariate" here is used to describe all clinical information about the patient, which are in general available at baseline. These clinical covariates comprise demographic information like sex, age etc., other anamnestic information, concomitant diseases, concomitant therapies, result of physical examinations, common laboratory parameters obtained, known properties of the target tumor, information quantifying the extent of malignant disease, clinical performance scores like ECOG or Karnofsky index, clinical disease staging, timing and result of pretreatments and disease history as well as all similar information, which may be associated with the clinical prognosis.

As used herein, the term "raw analysis" or "unadjusted analysis" refers to regression analyses, where over the considered biomarkers no additional clinical covariates were used in the regression model, neither as independent factors nor as stratifying covariate.

As used herein, the term "adjusted by covariates" refers to regression analyses, where over the considered biomarkers additional clinical covariates were used in the regression model, either as independent factors or as stratifying covariate.

As used herein, the term "univariate" refers to regression models or graphical approaches where as independent variable only one of the target biomarkers is part of the model. These univariate models can be considered with and without additional clinical covariates.

As used herein, the term "multivariate" refers to regression models or graphical approaches where as independent variables more than one of the target biomarkers are part of the model.

These multivariate models can be considered with and without additional clinical covariates.

"Nucleotides" are "nucleosides" that further include a phosphate group covalently linked to the sugar portion of the nucleoside. For those "nucleosides" that include a pentofuranosyl sugar, the phosphate group can be linked to either the 2',3'or 5' hydroxyl moiety of the sugar. A "nucleotide" is the "monomeric unit" of an "oligonucleotide", more generally denoted herein as an "oligomeric compound", or a "polynucleotide", more generally denoted as a "polymeric compound". Another general expression therefor is desoxyribonucleic acid (DNA) and ribonucleic acid (RNA). As used herein the term "polynucleotide" is synonymous with "nucleic acid."

As used herein, the term "probe" refers to synthetically or biologically produced nucleic acids (DNA or RNA) which, by design or selection, contain specific nucleotide sequences that allow them to hybridize under defined predetermined stringencies specifically (i.e., preferentially) to "nucleic acids". A "probe" can be identified as a "capture probe" meaning that it "captures" the nucleic acid so that it can be separated from undesirable materials which might obscure its detection. Once separation is accomplished, detection of the captured "target nucleic acid" can be achieved using a suitable procedure. "Capture probes" are often already attached to a solid phase. According to the present invention, the term hybridization under "stringent conditions" is given the same meaning as in Sambrook et al. (Molecular Cloning, A Laboratory Manual, Cold Spring Harbor Laboratory Press (1989), paragraph 1.101-1.104). Preferably, a "stringent hybridization" is the case when a hybridization signal is still detectable after washing for 1 h with 1×SSC and 0.1% SDS at 50° C., preferably at 55° C., more preferably at 62° C., and most preferably at 68° C., and more preferably for 1 hour with 0.2×SSC and 0.1% SDS at 50°, preferably at 55° C., more preferably at 62°, and most preferably at 68° C. The composition of the SSC buffer is described in Sambrook et al. (Molecular Cloning, A Laboratory Manual, Cold Spring Harbor Laboratory Press (1989)).

As used herein, a "transcribed polynucleotide" is a polynucleotide (e.g an RNA, a cDNA, or an analog of one of an RNA or cDNA) which is complementary to or homologous with all or a portion of a mature RNA made by transcription of a gene, such as the marker gene of the invention, and normal post-transcriptional processing (e.g. splicing), if any, of the transcript. The term "cDNA" is an abbreviation for complementary DNA, the single-stranded or double-stranded DNA copy of a mRNA. The term "mRNA" is an abbreviation for messenger RNA—the RNA that serves as a template for protein synthesis.

As used herein, the term "marker gene" or "biomarker gene" is meant to include a gene which is useful according to this invention for determining the progression of cancer in a patient, particularly in a breast cancer patient.

As used herein, the term "marker polynucleotide" or "biomarker polynucleotide" is meant to include a nucleotide transcript (hnRNA or mRNA) encoded by a marker gene according to the invention, or cDNA derived from the nucleotide transcript, or a segment of said transcript or cDNA.

As used herein, the term "marker protein," "marker polypeptide," "biomarker protein," or "biomarker polypeptide" is meant to include a protein or polypeptide encoded by a marker gene according to the invention or to a fragment thereof.

As used herein, the term "marker" and "biomarker" are used interchangeably and refer to a marker gene, marker polynucleotide, or marker protein as defined above.

As used herein, the term "gene product" refers to a marker polynucleotide or marker protein encoded by a marker gene.

The expression of a marker gene "significantly" differs from the level of expression of the marker gene in a reference sample if the level of expression of the marker gene in a sample from the patient differs from the level in a sample from the reference subject by an amount greater than the standard error of the assay employed to assess expression, and preferably at least 10%, and more preferably 25%, 50%, 75%, 100%, 125%, 150%, 175%, 200%, 300%, 400%, 500% or 1,000% of that amount. Alternatively, expression of the marker gene in the patient can be considered "significantly" lower than the level of expression in a control subject if the level of expression in a sample from the patient is lower than the level in a sample from the control subject by an amount greater than the standard error of the assay employed to assess expression, and preferably at least 10%, and more preferably 25%, 50%, 75%, 100%, 125%, 150%, 175%, 200%, 300%, 400%, 500% or 1,000% that amount.

A marker polynucleotide or a marker protein "corresponds to" another marker polynucleotide or marker protein if it is related thereto, and in preferred embodiments is identical thereto.

The terms "level of expression" or "expression level" are used interchangeably and generally refer to the amount of a polynucleotide or an amino acid product or protein in a biological sample. "Expression" generally refers to the process by which gene encoded information is converted into the structures present and operating in the cell. Therefore, according to the invention "expression" of a gene may refer to transcription into a polynucleotide, translation into a protein or even posttranslational modification of the protein. Fragments of the transcribed polynucleotide, the translated protein or the postranslationally modified protein shall also be regarded as expressed whether they originate from a transcript generated by alternative splicing, a degraded transcript or from a posttranslational processing of the protein, e.g. by proteolysis. "Expressed genes" include those that are transcribed into a polynucleotide as mRNA and then translated into a protein; and also include expressed genes that are transcribed into RNA but not translated into a protein (for example, transfer and ribosomal RNAs).

The term "overexpression" or "increased expression" refers to an upward deviation in levels of expression as compared to the baseline expression level in a sample used as a control.

The term "underexpression" or "decreased expression" refers to a downward deviation in levels of expression as compared to the baseline expression level in a sample used as a control.

The term "amphiregulin" relates to a gene that encodes a protein and to the protein itself that is a member of the epidermal growth factor family. It is an autocrine growth factor as well as a mitogen for astrocytes, Schwann cells, and fibroblasts. It is related to epidermal growth factor (EGF) and transforming growth factor alpha (TGF-alpha). This protein interacts with the EGF/TGF-alpha receptor to promote the growth of normal epithelial cells and inhibits the growth of certain aggressive carcinoma cell lines. According to the invention, the amino acid sequence of amphiregulin is the amino acid sequence according to SEQ ID NO: 1. According to the invention, the nucleic acid sequence of the "amphiregulin" cDNA is the nucleic acid sequence according to SEQ ID NO: 5 which is accessible at GenBank with the accession number NM_001657.

The term "transforming growth factor alpha" relates to a gene that encodes a protein and to the protein itself that is a member of the family of transforming growth factors (TGFs). These are biologically active polypeptides that reversibly confer the transformed phenotype on cultured cells. "Transforming growth factor-alpha" shows about 40% sequence homology with epidermal growth factor and competes with EGF for binding to the EGF receptor, stimulating its phosphorylation and producing a mitogenic response. According to the invention, the amino acid sequence of "Transforming growth factor-alpha" is the amino acid sequence according to SEQ ID NO: 3. According to the invention, the nucleic acid sequence of the "transforming growth factor-alpha" cDNA is the nucleic acid sequence according to SEQ ID NO: 7 which is accessible at GenBank with the accession number NM_003236.

The term "epidermal growth factor" relates to a gene that encodes a protein and to the protein itself that is a member of the family of growth factors. "Epidermal growth factor (EGF)" has a profound effect on the differentiation of specific cells in vivo and is a potent mitogenic factor for a variety of cultured cells of both ectodermal and mesodermal origin. The EGF precursor is believed to exist as a membrane-bound molecule which is proteolytically cleaved to generate the 53-amino acid peptide hormone that stimulates cells to divide. According to the invention, the amino acid sequence of "Epidermal growth factor" is the amino acid sequence according to SEQ ID NO: 2. According to the invention, the nucleic acid sequence of the "Epidermal growth factor (EGF)" cDNA is the nucleic acid sequence according to SEQ ID NO: 6 which is accessible at GenBank with the accession number NM_001963. The "Epidermal Growth Factor Receptor" abbreviated as EGFR, a 170-kD glycoprotein, is composed of an N-terminus extracellular domain, a hydrophobic transmembrane domain, and a C-terminus intracellular region containing the kinase domain. The mRNA has different variants translated into different receptor proteins. According to the invention, the amino acid sequence of the "Epidermal growth factor receptor" is the amino acid sequence according to SEQ ID NO: 11 (transcript variant 1; GenBank accession number NM_005228), SEQ ID NO: 12 (transcript variant 2; GenBank accession number NM_201282), SEQ ID NO: 13 (transcript variant 3; GenBank accession number NM_201283), or SEQ ID NO: 14 (transcript variant 4; GenBank accession number NM_201284). EGFR, encoded by the erbB1 gene, has been causally implicated in human malignancy. In particular, increased expression of EGFR has been observed in breast, bladder, lung, head, neck and stomach cancer as well as glioblastomas. EGFR ligand-induced dimerization activates the intrinsic RTK domain (an Src homology domain 1, SH1), resulting in autophosphorylation on six specific EGFR tyrosine residues in the noncatalytic tail of the cytoplasmic domain. The cellular effects of EGFR activation in a cancer cell include increased proliferation, promotion of cell motility, adhesion, invasion, angiogenesis, and enhanced cell survival by inhibition of apoptosis. Activated EGFR induces tumor cell proliferation through stimulation of the mitogen-activated protein kinase (MAPK) cascade.

The terms "human neu", "c-erbB-2", "erbB2", "erbB-2", "HER-2/neu", "HER-2" and "HER2" are used interchangeably herein. These terms relate to a gene that encodes a protein and to the protein itself that is a member of the family of the epidermal growth factor (EGF) receptor family of receptor tyrosine kinases. This protein has no ligand binding domain of its own and therefore cannot bind growth factors. However, it does bind tightly to other ligand-bound EGF receptor family members to form a heterodimer, stabilizing ligand binding and enhancing kinase-mediated activation of downstream signalling pathways, such as those involving mitogen-activated protein kinase and phosphatidylinositol-3 kinase. Allelic variations at amino acid positions 654 and 655 of isoform a (positions 624 and 625 of isoform b) have been reported, with the most common allele, Ile654/Ile655 being preferred according to the invention. Amplification and/or overexpression of this gene has been reported in numerous cancers, including breast and ovarian tumors. Alternative splicing results in several additional transcript variants, some encoding different isoforms and others that have not been fully characterized. According to the invention, the amino acid sequence of HER2 is the amino acid sequence according to SEQ ID NO: 4. According to the invention, the nucleic acid sequence of the "HER2" cDNA is the nucleic acid sequence according to SEQ ID NO: 8 which is accessible at GenBank with the accession number NM_004448.2.

The "extracellular domain of HER2" or "shed extracellular domain of HER2" or "HER2-ECD" is a glycoprotein of between 97 and 115 kDa which corresponds substantially to the extracellular domain of the human HER2 gene product. It can be referred to as p105 (Zabrecky, J. R. et al., J. Biol. Chem. 266 (1991) 1716-1720; U.S. Pat. No. 5,401,638; U.S. Pat. No. 5,604,107). The quantitation and detection of the extracellular domain of HER2 is described in U.S. Pat. No. 5,401,638 and U.S. Pat. No. 5,604,107.

The term "HER3" stands for another member of the epidermal growth factor receptor (EGFR) family of receptor tyrosine kinases. This membrane-bound protein has not an active kinase domain. The protein can bind ligands but not transmit a signal into the cell. It forms heterodimers with other EGF receptor family members which do have kinase activity which leads to cell proliferation or differentiation. Amplification of this gene and/or overexpression of its protein is found in numerous cancers. According to the invention, the amino acid sequence of the "HER3" cDNA is the amino acid sequence according to SEQ ID NO: 9 which is accessible at GenBank from the translation of the nucleic acid sequence of HER3 with the accession number NM_001005915. According to the invention, the nucleic acid sequence of the "HER3" cDNA is the nucleic acid sequence according to SEQ ID NO: 10 which is accessible at GenBank with the accession number NM_001005915.

The term "antibody" herein is used in the broadest sense and specifically covers intact monoclonal antibodies, polyclonal antibodies, and multispecific antibodies (e.g., bispecific antibodies) formed from at least two intact antibodies, and antibody fragments, so long as they exhibit the desired biological activity of an antibody.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler, G. et al., Nature 256 (1975) 495-497, or may be made by recombinant DNA methods (see, e.g., U.S. Pat. No. 4,816,567). "Antibody fragments" comprise a portion of an intact antibody.

An antibody "which binds" an antigen of interest according to the invention is one capable of binding that antigen with sufficient affinity such that the antibody is useful in detecting the presence of the antigen. One antibody according to the invention binds human HER2 and does not (significantly) cross-react with other proteins. In such embodiments, the extent of binding of the antibody to other proteins will be less than 10% as determined by fluorescence activated cell sorting (FACS) analysis or radioimmunoprecipitation (RIA).

Dimerization—the pairing of receptors—is essential to the signaling activity of all HER receptors. According to the invention, the term "HER dimerization inhibitor" or preferably "HER2 heterodimerization inhibitor" refers to a therapeutic agent that binds to HER2 and inhibits HER2 heterodimerization. These are preferably antibodies, preferably monoclonal antibodies, more preferably humanized antibodies that bind to HER2 and inhibit HER2 heterodimerization. Examples of antibodies that bind HER2 include 4D5, 7C2, 7F3 or 2C4 as well as humanized variants thereof, including huMAb4D5-1, huMAb4D5-2, huMAb4D5-3, huMAb4D5-4, huMAb4D5-5, huMAb4D5-6, huMAb4D5-7 and huMAb4D5-8 as described in Table 3 of U.S. Pat. No. 5,821,337; and humanized 2C4 mutant numbers 560, 561, 562, 568, 569, 570, 571, 574, or 56869 as described in WO 01/00245. 7C2 and 7F3 and humanized variants thereof are described in WO 98/17797. The term "HER dimerization inhibitor" or "HER2 heterodimerization inhibitor" shall not apply to Trastuzumab monoclonal antibodies commercially available as "Herceptin®" as the mechanism of action is different and as Trastuzumab does not inhibit HER dimerization.

Preferred throughout the application is the "antibody 2C4", in particular the humanized variant thereof (WO 01/00245; produced by the hybridoma cell line deposited with the American Type Culture Collection; Manassass, Va., USA under ATCC HB-12697), which binds to a region in the extracellular domain of HER2 (e.g., any one or more residues in the region from about residue 22 to about residue 584 of HER2, inclusive). The "epitope 2C4" is the region in the extracellular domain of ErbB2 to which the antibody 2C4 binds. The expression "monoclonal antibody 2C4" refers to an antibody that has antigen binding residues of, or derived from, the murine 2C4 antibody of the Examples in WO 01/00245. For example, the monoclonal antibody 2C4 may be murine monoclonal antibody 2C4 or a variant thereof, such as humanized antibody 2C4, possessing antigen binding amino acid residues of murine monoclonal antibody 2C4. Examples of humanized 2C4 antibodies are provided in Example 3 of WO 01/00245. Unless indicated otherwise, the expression "rhuMAb 2C4" when used herein refers to an antibody comprising the variable light (VL) and variable heavy (VH) sequences of SEQ ID Nos. 3 and 4 of WO 01/00245, respectively, fused to human light and heavy IgG1 (non-A allotype) constant region sequences optionally expressed by a Chinese Hamster Ovary (CHO) cell. Preferred embodiments of WO 01/00245 are preferred herein as well. The humanized antibody 2C4 is also called Pertuzumab.

A "kit" is any manufacture (e.g a package or container) comprising at least one reagent, e.g a probe, for specifically detecting a marker gene or protein of the invention. The manufacture is preferably promoted, distributed, or sold as a unit for performing the methods of the present invention.

The verbs "determine" and "assess" shall have the same meaning and are used interchangeably throughout the application.

Conventional techniques of molecular biology and nucleic acid chemistry, which are within the skill of the art, are explained in the literature. See, for example, Sambrook, J. et al., Molecular Cloning: A Laboratory Manual, Cold Spring Harbor Laboratory Press, Cold Spring Harbor, N.Y., 1989; Gait, M. J. (ed.), Oligonucleotide synthesis—a practical approach, IRL Press Limited, 1984; Hames, B. D. and Higgins, S. J. (eds.), Nucleic acid hybridisation—a practical approach, IRL Press Limited, 1985; and a series, Methods in Enzymology, Academic Press, Inc., all of which are incorporated herein by reference. All patents, patent applications, and publications mentioned herein, both supra and infra, are hereby incorporated by reference in their entirety.

As used herein, the general form of a prediction rule consists in the specification of a function of one or multiple biomarkers potentially including clinical covariates to predict response or non-response, or more generally, predict benefit or lack of benefit in terms of suitably defined clinical endpoints.

The simplest form of a prediction rule consists of an univariate model without covariates, where the prediction is determined by means of a cutoff or threshold. This can be phrased in terms of the Heaviside function for a specific cutoff c and a biomarker measurement x, where the binary prediction A or B is to be made, then If $H(x-c)=0$ then predict $A$.

If $H(x-c)=1$ then predict $B$.

This is the simplest way of using univariate biomarker measurements in prediction rules. If such a simple rule is sufficient, it allows for a simple identification of the direction of the effect, i.e. whether high or low expression levels are beneficial for the patient.

The situation can be more complicated if clinical covariates need to be considered and/or if multiple biomarkers are used in multivariate prediction rules. In order to illustrate the issues here are two hypothetical examples:

Covariate Adjustment (Hypothetical Example)

For a biomarker X it is found in a clinical trial population that high expression levels are associated with a worse prognosis (univariate analysis). A closer analysis shows that there are two tumor types in the population, one of which possess a worse prognosis than the other one and at the same time the biomarker expression for this tumor group is generally higher. An adjusted covariate analysis reveals that for each of the tumor types the relation of clinical benefit and prognosis is reversed, i.e. within the tumor types, lower expression levels are associated with better prognosis. The overall opposite effect was masked by the covariate tumor type—and the covariate adjusted analysis as part of the prediction rule reversed the direction.

Multivariate Prediction (Hypothetical Example)

For a biomarker X it is found in a clinical trial population that high expression levels are slightly associated with a worse prognosis (univariate analysis). For a second biomarker Y a similar observation was made by univariate analysis. The combination of X and Y revealed that a good prognosis is seen if both biomarkers are low. This makes the rule to predict benefit if both biomarkers are below some cutoffs (AND— connection of a Heaviside prediction function). For the combination rule there is no longer a simple rule phraseable in an univariate sense. E.g. having low expression levels in X will not automatically predict a better prognosis.

These simple examples show that prediction rules with and without covariates cannot be judged on the univariate level of each biomarker. The combination of multiple biomarkers plus a potential adjustment by covariates does not allow to assign simple relationships towards single biomarkers.

In one embodiment of the invention, a method of predicting the response to a treatment with a HER inhibitor, preferably a HER dimerization inhibitor, in a patient comprises the steps of:
  (a) determining the expression level or amount of one or more biomarkers in a biological sample from a patient wherein the biomarker or biomarkers are selected from the group consisting of:
    (1) transforming growth factor alpha;
    (2) HER2;
    (3) amphiregulin; and
    (4) epidermal growth factor;
  (b) determining whether the expression level or amount assessed in step (a) is above or below a certain quantity that is associated with an increased or decreased clinical benefit to a patient; and (c) predicting the response to the treatment with the HER inhibitor in the patient by evaluating the results of step (b).

In a more particular embodiment of the above method, the expression level of the transforming growth factor alpha biomarker is determined in combination with one or more biomarkers selected from the group consisting of epidermal growth factor, amphiregulin, and HER2. In another more particular embodiment of the above method, the expression level of the HER2 biomarker is determined in combination with one or more biomarkers selected from the group consisting of epidermal growth factor, transforming growth factor alpha, and amphiregulin. In another more particular embodiment of the above method, the expression level of the epidermal growth factor biomarker is determined in combination with one or more biomarkers selected from the group consisting of amphiregulin, transforming growth factor alpha, and HER2. In another more particular embodiment of the above method, an amphiregulin biomarker is assessed in combination with one or more biomarkers selected from the group consisting of epidermal growth factor, transforming growth factor alpha, and HER2.

The "quantity that is associated with an increased or decreased clinical benefit to a patient" of the above method is preferably a value expressed in mass/volume for blood serum or blood plasma or mass/mass for tumor tissue. It can be measured by methods known to the expert skilled in the art and also disclosed by this invention. If the expression level or amount determined in step (a) is above or below a certain quantity or value, the response to the treatment can be determined.

With respect to the quantity in blood serum for the transforming growth factor alpha marker protein, a range between 2.0-10.0 pg/ml, preferably a range between 2.0-5.0 pg/ml, and more preferably about 3.5 pg/ml may be favorable for progression free survival and overall survival when treatment with a HER inhibitor is considered. See FIG. 7. Thus, in a preferred embodiment, the quantity of transforming growth factor alpha marker protein in the blood serum of a patient is within one of the foregoing ranges for predicting a good response to treatment with a HER inhibitor in the patient.

With respect to the quantity in blood serum for the HER2 marker protein (preferably the soluble HER2 extracellular domain (HER2-ECD)), a range between 12-22 ng/ml, preferably about 18 ng/ml, may be favorable for progression free survival and overall survival when treatment with a HER inhibitor is considered. See FIG. 7. Thus, in a preferred embodiment, the quantity of HER2 marker protein in the blood serum of a patient is within the foregoing range for predicting a good response to treatment with a HER inhibitor in the patient.

With respect to the quantity in blood serum for the epidermal growth factor marker protein, a range between 100-250 pg/ml, preferably about 150 pg/ml, may be favorable for progression free survival and overall survival when treatment with a HER inhibitor is considered. See FIG. 7. Thus, in a preferred embodiment, the quantity of epidermal growth factor marker protein in the blood serum of a patient is within the foregoing range for predicting a good response to treatment with a HER inhibitor in the patient.

With respect to the quantity in blood serum for the amphiregulin marker protein, a range between 6-15 pg/ml, preferably about 12 pg/ml, may be favorable for progression free survival and overall survival when treatment with a HER inhibitor is considered. See FIG. 7. Thus, in a preferred embodiment, the quantity of amphiregulin marker protein in the blood serum of a patient is within the foregoing range for predicting a good response to treatment with a HER inhibitor in the patient.

Since the marker genes, in particular in serum, may be used in multiple-marker prediction models potentially including other clinical covariates, the direction of a beneficial effect of a single marker gene within such models cannot be determined in a simple way, and may contradict the direction found in univariate analyses, i.e. the situation as described for the single marker gene.

More preferably, in the method according to the invention, the quantity or value (below or above which is associated with an increased or decreased clinical benefit) is determined by:
(1) determining the expression level or amount of a biomarker or combination of biomarkers in a plurality of biological samples from patients before treatment with the HER inhibitor,
(2) treating the patients with the HER inhibitor,
(3) determining the clinical benefit of each patient; and
(4) correlating the clinical benefit of the patients treated with the HER inhibitor to the expression level or amount of the biomarker or combination of biomarkers.

The "quantity" is preferably a value expressed in mass/volume for blood serum or blood plasma or mass/mass for tumor tissue.

The present invention also considers mutants or variants of the marker genes according to the present invention and used in the methods according to the invention. In those mutants or variants the native sequence of the marker gene is changed by substitutions, deletions or insertions. "Native sequence" refers to an amino acid or nucleic acid sequence which is identical to a wild-type or native form of a marker gene or protein.

The present invention also considers mutants or variants of the proteins according to the present invention and used in the methods according to the invention. "Mutant amino acid sequence," "mutant protein" or "mutant polypeptide" refers to a polypeptide having an amino acid sequence which varies from a native sequence or is encoded by a nucleotide sequence intentionally made variant from a native sequence. "Mutant protein," "variant protein" or "mutein" means a protein comprising a mutant amino acid sequence and includes polypeptides which differ from the amino acid sequence of the native protein according to the invention due to amino acid deletions, substitutions, or both.

The present invention also considers a method of predicting the response to a treatment with a combination of a HER inhibitor and another substance or agent as a chemotherapeutic agent or a therapeutic antibody used for treating cancer. The chemotherapeutic agent may be e.g. gemcitabine (Gemzar®; chemical name: 2',2'-difluorodeoxycytidine (dFdC)), carboplatin (diammine-(cyclobutane-1,1-dicarboxylato(2-)-O,O')-platinum), or paclitaxel (Taxol®, chemical name: β-(benzoylamino)-α-hydroxy-,6,12b-bis(acetyloxy)-12-(benzoyloxy)-2a,3,4,4a,5,6,9,10,11,12,12a,12b-dodecahydro-4,11-dihydroxy-4a,8,13,13-tetramethyl-5-oxo-7,11-methano-1H-cyclodeca(3,4)benz(1,2-b)oxet-9-yl ester,(2aR-(2a-α,4-β,4a-β,6-β, 9-α(α-R*,β-S*),11-α,12-α, 12α-α,2b-α))-benzenepropanoic acid); or transtuzumab; or erlotinib.

In a preferred embodiment of the invention, the biological sample is blood serum, blood plasma or tumor tissue. Tumor tissue may be formalin-fixed paraffin embedded tumor tissue or fresh frozen tumor tissue.

In another preferred embodiment of the invention, the HER dimerization inhibitor inhibits heterodimerization of HER2 with EGFR or HER3, or HER4. Preferably, the HER dimerization inhibitor is an antibody, preferably the antibody 2C4. Preferred throughout the application is the "antibody 2C4", in particular the humanized variant thereof (WO 01/00245; produced by the hybridoma cell line deposited with the American Type Culture Collection, Manassass, Va., USA under ATCC HB-12697), which binds to a region in the extracellular domain of HER2 (e.g., any one or more residues in the region from about residue 22 to about residue 584 of HER2, inclusive). Examples of humanized 2C4 antibodies are provided in Example 3 of WO 01/00245. The humanized antibody 2C4 is also called Pertuzumab.

In still another preferred embodiment of the invention, the patient is a cancer patient, preferably a breast cancer, ovarian cancer, lung cancer or prostate cancer patient. The breast cancer patient is preferably a metastatic breast cancer patient or a HER2 low expressing breast or metastatic breast cancer patient, or a HER2 high expressing breast or metastatic breast cancer patient. The ovarian cancer patient is preferably a metastatic ovarian cancer patient. The lung cancer patient is preferably a non-small cell lung cancer (NSCLC) patient.

It is preferred that two, three or all four marker genes, marker polynucleotides or marker proteins are used in combination, i.e. used in all disclosed embodiments of the invention or methods, uses or kits according to the invention. The following are preferred combinations of biomarkers in which the level of expression or amounts are determined in accordance with the invention:

In one particular embodiment, a transforming growth factor alpha biomarker is assessed in combination with one or more biomarkers selected from the group consisting of epidermal growth factor, amphiregulin, and HER2. In another particular embodiment, a HER2 biomarker is assessed in combination with one or more biomarkers selected from the group consisting of epidermal growth factor, transforming growth factor alpha, and amphiregulin. In another particular embodiment, a epidermal growth factor biomarker is assessed in combination with one or more biomarkers selected from the group consisting of amphiregulin, transforming growth factor alpha, and HER2. In another particular embodiment, an amphiregulin biomarker is assessed in combination with one or more biomarkers selected from the group consisting of epidermal growth factor, transforming growth factor alpha, and HER2.

In a particularly preferred embodiment of the invention, the combination of biomarkers consists of:
    the transforming growth factor alpha and the HER2 biomarkers, or
    the transforming growth factor alpha and the EGF biomarkers, or
    the amphiregulin, the epidermal growth factor, the transforming growth factor alpha and the HER2 biomarkers, In a preferred embodiment of the invention, the level of expression of the marker gene or the combination of marker genes in the sample is assessed by detecting the level of expression of a marker protein or a fragment thereof or a combination of marker proteins or fragments thereof encoded by the marker gene or the combination of marker genes. Preferably, the level of expression of the marker protein or the fragment thereof or the combination of marker proteins or the fragments thereof is detected using a reagent which specifically binds with the marker protein or the fragment thereof or the combination of marker proteins or the fragments thereof. Preferably, the reagent is selected from the group consisting of an antibody, a fragment of an antibody, and an antibody derivative.

There are many different types of immunoassays which may be used in the method of the present invention, e.g. enzyme linked immunoabsorbent assay (ELISA), fluorescent immunosorbent assay (FIA), chemical linked immunosorbent assay (CLIA), radioimmuno assay (RIA), and immunoblotting. For a review of the different immunoassays which may be used, see: Lottspeich and Zorbas (eds.), Bioanalytik, $1^{st}$ edition 1998, Spektrum Akademischer Verlag, Heidelberg, Berlin, Germany. Therefore, in yet another preferred embodiment of the invention, the level of expression is determined using a method selected from the group consisting of proteomics, flow cytometry, immunocytochemistry, immunohistochemistry, enzyme-linked immunosorbent assay, multi-channel enzyme-linked immunosorbent assay, and variations of these methods. Therefore more preferably, the level of expression is determined using a method selected from the group consisting of proteomics, flow cytometry, immunocytochemistry, immunohistochemistry, enzyme-linked immunosorbent assay, multi-channel enzyme-linked immunosorbent assay, and variations of these methods.

In another preferred embodiment of the invention, the fragment of the marker protein is the extracellular domain of the HER2 marker protein (HER2-ECD). Preferably, the extracellular domain of the HER2 marker protein has a molecular mass of approximately 105,000 Dalton. "Dalton" stands for a mass unit that is equal to the weight of a hydrogen atom, or $1.657 \times 10^{-24}$ grams.

In another preferred embodiment of the invention
    the amino acid sequence of the amphiregulin marker protein is the amino acid sequence SEQ ID NO: 1,
    the amino acid sequence of the epidermal growth factor marker protein is the amino acid sequence SEQ ID NO: 2,
    the amino acid sequence of the transforming growth factor alpha marker protein is the amino acid sequence SEQ ID NO: 3, or
    the amino acid sequence of the HER2 marker protein is the amino acid sequence SEQ ID NO: 4.

In another preferred embodiment of the invention, the quantity in blood serum for
    the transforming growth factor alpha marker protein is between 2.0 to 10.0 pg/ml, preferably about 3.5 pg/ml,
    the epidermal growth factor marker protein is between 100 to 250 pg/ml, preferably about 150 pg/ml, or
    the amphiregulin marker protein is between 6 to 15 pg/ml, preferably about 12 pg/ml.
    the HER2 marker protein is between 12 to 22 ng/ml, preferably about 18 ng/ml.

In still another preferred embodiment of the invention, the "quantity" in blood serum for the extracellular domain of the HER2 marker protein is between 12 to 22 ng/ml, preferably about 18 ng/ml.

In yet another preferred embodiment of the invention, the level of expression of the marker gene or the combination of marker genes in the biological sample is assessed by detecting the level of expression of a transcribed marker polynucleotide encoded by the marker gene or a fragment of the transcribed marker polynucleotide or of transcribed marker polynucleotides encoded by the combination of marker genes or fragments of the transcribed marker polynucleotide. Preferably, the transcribed marker polynucleotide is a cDNA, mRNA or hnRNA or wherein the transcribed marker polynucleotides are cDNA, mRNA or hnRNA.

Preferably, the step of detecting further comprises amplifying the transcribed polynucleotide. The amplification is performed preferably with the polymerase chain reaction which specifically amplifies nucleic acids to detectable amounts. Other possible amplification reactions are the Ligase Chain Reaction (LCR; Wu D. Y. and Wallace R. B., Genomics 4 (1989) 560-569; and Barany F., Proc. Natl. Acad. Sci. USA 88 (1991)189-193); Polymerase Ligase Chain Reaction (Barany F., PCR Methods and Applic. 1 (1991) 5-16); Gap-LCR (WO 90/01069); Repair Chain Reaction (EP 0439182 A2), 3SR (Kwoh, D. Y. et al., Proc. Natl. Acad. Sci. USA 86 (1989) 1173-1177; Guatelli, J. C. et al., Proc. Natl. Acad. Sci. USA 87 (1990) 1874-1878; WO 92/08808), and NASBA (U.S. Pat. No. 5,130,238). Further, there are strand displacement amplification (SDA), transcription mediated amplification (TMA), and Qβ-amplification (for a review see e.g. Whelen, A. C. and Persing, D. H., Annu. Rev. Microbiol. 50 (1996) 349-373; Abramson, R. D. and Myers T. W., Curr. Opin. Biotechnol. 4 (1993) 41-47). More preferably, the step of detecting is using the method of quantitative reverse transcriptase polymerase chain reaction.

Other suitable polynucleotide detection methods are known to the expert in the field and are described in standard textbooks as Sambrook J. et al., Molecular Cloning: A Laboratory Manual, Cold Spring Harbor Laboratory Press, Cold Spring Harbor, N.Y., 1989; and Ausubel, F. et al., Current Protocols in Molecular Biology, 1987, J. Wiley and Sons, NY. There may be also further purification steps before the polynucleotide detection step is carried out as e.g. a precipitation step. The detection methods may include but are not limited to the binding or intercalating of specific dyes as ethidiumbromide which intercalates into the double-stranded polynucleotides and changes their fluorescence thereafter. The purified polynucleotide may also be separated by electrophoretic methods optionally after a restriction digest and visualized thereafter. There are also probe-based assays which exploit the oligonucleotide hybridisation to specific sequences and subsequent detection of the hybrid. It is also possible to sequence the DNA after further steps known to the expert in the field. The preferred template-dependent DNA polymerase is Taq polymerase.

In yet another preferred embodiment of the invention, the level of expression of the marker gene is assessed by detecting the presence of the transcribed marker polynucleotide or the fragment thereof in a sample with a probe which anneals with the transcribed marker polynucleotide or the fragment thereof under stringent hybridization conditions or the level of expression of the combination of the marker genes in the samples is assessed by detecting the presence of transcribed marker polynucleotides or the fragments thereof in a sample with probes which anneal with the transcribed marker polynucleotides or the fragments thereof under stringent hybridization conditions. This method may be performed in a homogeneous assay system. An example for a "homogeneous" assay system is the TaqMan® system that has been detailed in U.S. Pat. No. 5,210,015, U.S. Pat. No. 5,804,375 and U.S. Pat. No. 5,487,972. Briefly, the method is based on a double-labelled probe and the 5'-3' exonuclease activity of Taq DNA polymerase. The probe is complementary to the target sequence to be amplified by the PCR process and is located between the two PCR primers during each polymerisation cycle step. The probe has two fluorescent labels attached to it. One is a reporter dye, such as 6-carboxyfluorescein (FAM), which has its emission spectra quenched by energy transfer due to the spatial proximity of a second fluorescent dye, 6-carboxy-tetramethyl-rhodamine (TAMRA). In the course of each amplification cycle, the Taq DNA polymerase in the process of elongating a primed DNA strand displaces and degrades the annealed probe, the latter due to the intrinsic 5'-3' exonuclease activity of the polymerase. The mechanism also frees the reporter dye from the quenching activity of TAMRA. As a consequence, the fluorescent activity increases with an increase in cleavage of the probe, which is proportional to the amount of PCR product formed. Accordingly, an amplified target sequence is measured by detecting the intensity of released fluorescence label. Another example for "homogeneous" assay systems are provided by the formats used in the LightCycler® instrument (see e.g. U.S. Pat. No. 6,174,670), some of them sometimes called "kissing probe" formats. Again, the principle is based on two interacting dyes which, however, are characterized in that the emission wavelength of a donor-dye excites an acceptor-dye by fluorescence resonance energy transfer. The COBAS® AmpliPrep instrument (Roche Diagnostics GmbH, D-68305 Mannheim, Germany) was recently introduced to expand automation by isolating target sequences using biotinylated sequence-specific capture probes along with streptavidin-coated magnetic particles (Jungkind, D., J. Clin. Virol. 20 (2001) 1-6; Stelzl, E. et al., J. Clin. Microbiol. 40 (2002) 1447-1450). It has lately been joined by an additional versatile tool, the Total Nucleic Acid Isolation (TNAI) Kit (Roche Diagnostics). This laboratory-use reagent allows the generic, not sequence-specific isolation of all nucleic acids from plasma and serum on the COBAS® AmpliPrep instrument based essentially on the method developed by Boom, R. et al., J. Clin. Microbiol. 28 (1990) 495-503.

In another preferred embodiment of the invention, the nucleic acid sequence of the amphiregulin marker polynucleotide is the nucleic acid sequence SEQ ID NO: 5, the nucleic acid sequence of the epidermal growth factor marker polynucleotide is the nucleic acid sequence SEQ ID NO: 6, the nucleic acid sequence of the transforming growth factor alpha marker polynucleotide is the nucleic acid sequence SEQ ID NO: 7, or the nucleic acid sequence of the HER2 marker polynucleotide is the nucleic acid sequence SEQ ID NO: 8.

In another embodiment of the invention, a probe that hybridizes with the epidermal growth factor, transforming growth factor alpha or HER2 marker polynucleotide under stringent conditions or an antibody that binds to the epidermal growth factor, transforming growth factor alpha or HER2 marker protein is used for predicting the response to treatment with a HER inhibitor in a patient or a probe that hybridizes with the amphiregulin, epidermal growth factor, transforming growth factor alpha or HER2 marker polynucleotide under stringent conditions or an antibody that binds to the amphiregulin, epidermal growth factor, transforming growth factor alpha or HER2 marker protein is used for selecting a composition for inhibiting the progression of disease in a patient. The disease is preferably cancer and the patient is preferably a cancer patient as disclosed above.

In another embodiment of the invention, a kit comprising a probe that anneals with the amphiregulin, epidermal growth factor, transforming growth factor alpha or HER2 marker polynucleotide under stringent conditions or an antibody that binds to the amphiregulin, epidermal growth factor, transforming growth factor alpha or HER2 marker protein is provided. Such kits known in the art further comprise plastics ware which can be used during the amplification procedure as e.g. microtitre plates in the 96 or 384 well format or just ordinary reaction tubes manufactured e.g. by Eppendorf, Hamburg, Germany and all other reagents for carrying out the method according to the invention, preferably an immunoassay, e.g. enzyme linked immunoabsorbent assay (ELISA), fluorescent immunosorbent assay (FIA), chemical linked immunosorbent assay (CLIA), radioimmuno assay (RIA), and immunoblotting. For a review of the different immunoassays and reagents which may be used, see: Lottspeich and Zorbas (eds.), Bioanalytik, 1$^{st}$ edition, 1998, Spektrum Akademischer Verlag, Heidelberg, Berlin, Germany. Preferably combinations of the probes or antibodies to the various marker polynucleotides or marker proteins are provided in the form of kit as the preferred combinations of the marker polynucleotides or marker proteins as disclosed above.

In another embodiment of the invention, a method of selecting a composition for inhibiting the progression of disease in a patient is provided, the method comprising:
(a) separately exposing aliquots of a biological sample from a cancer patient in the presence of a plurality of test compositions;
(b) comparing the level of expression of one or more biomarkers selected from the group consisting of amphiregulin, epidermal growth factor, transforming growth factor alpha and HER2 in the aliquots of the biological sample contacted with the test compositions and the level of expression of such biomarkers in an aliquot of the biological sample not contacted with the test compositions; and
(c) selecting one of the test compositions which alters the level of expression of the biomarker or biomarkers in the aliquot containing that test composition relative to the aliquot not contacted with the test composition wherein an at least 10% difference between the level of expression of the biomarker or biomarkers in the aliquot of the biological sample contacted with the test composition and the level of expression of the corresponding biomarker or biomarkers in the aliquot of the biological sample not contacted with the test composition is an indication for the selection of the test composition. The disease is preferably cancer and the patient is preferably a cancer patient as disclosed above.

In another embodiment of the invention, a method of selecting a composition for inhibiting the progression of disease in a patient is provided, the method comprising:
(a) separately exposing aliquots of a biological sample from a cancer patient in the presence of a plurality of test compositions;
(b) comparing the level of expression of one or more biomarkers selected from the group consisting of the amphiregulin, epidermal growth factor, transforming growth factor alpha and HER2 in the aliquots of the biological sample contacted with the test compositions and the level of expression of such biomarkers in an aliquot of the biological sample not contacted with the test compositions; and
(c) selecting one of the test compositions which alters the level of expression of the biomarker or biomarkers in the aliquot containing that test composition relative to the aliquot not contacted with the test composition wherein an at least 10% difference between the level of expression of the biomarker or biomarkers in the aliquot of the biological sample contacted with the test composition and the level of expression of the corresponding biomarker or biomarkers in the aliquot of the biological sample not contacted with the test composition is an indication for the selection of the test composition. The disease is preferably cancer and the patient is preferably a cancer patient as disclosed above.

The expression of a marker gene "significantly" differs from the level of expression of the marker gene in a reference sample if the level of expression of the marker gene in a sample from the patient differs from the level in a sample from the reference subject by an amount greater than the standard error of the assay employed to assess expression, and preferably at least 10%, and more preferably 25%, 50%, 75%, 100%, 125%, 150%, 175%, 200%, 300%, 400%,500% or 1,000% of that amount. Alternatively, expression of the marker gene in the patient can be considered "significantly" lower than the level of expression in a reference subject if the level of expression in a sample from the patient is lower than the level in a sample from the reference subject by an amount greater than the standard error of the assay employed to assess expression, and preferably at least 10%, and more preferably 25%, 50%, 75%, 100%, 125%, 150%, 175%, 200%, 300%, 400%, 500% or 1,000% that amount. The difference of the level of expression be up to 10,000 or 50,000%. The difference of the level of expression is preferably between 10% to 10,000%, more preferably 25% to 10,000%, 50% to 10,000%, 100% to 10,000%, even more preferably 25% to 5,000%, 50% to 5,000%, 100% to 5,000%.

In another embodiment of the invention, a method of identifying a candidate agent is provided said method comprising:
(a) contacting an aliquot of a biological sample from a cancer patient with the candidate agent and determining the level of expression of one or more biomarkers selected from the group consisting of amphiregulin, epidermal growth factor, transforming growth factor alpha and HER2 in the aliquot;
(b) determining the level of expression of a corresponding biomarker or biomarkers in an aliquot of the biological sample not contacted with the candidate agent;
(c) observing the effect of the candidate agent by comparing the level of expression of the biomarker or biomarkers in the aliquot of the biological sample contacted with the candidate agent and the level of expression of the corresponding biomarker or biomarkers in the aliquot of the biological sample not contacted with the candidate agent; and
(d) identifying said agent from said observed effect, wherein an at least 10% difference between the level of expression of the biomarker gene or combination of biomarker genes in the aliquot of the biological sample contacted with the candidate agent and the level of expression of the corresponding biomarker gene or combination of biomarker genes in the aliquot of the biological sample not contacted with the candidate agent is an indication of an effect of the candidate agent.

In still another embodiment of the invention, a method of identifying a candidate agent is provided said method comprising:
(a) contacting an aliquot of a biological sample from a cancer patient with the candidate agent and determining the level of expression in the aliquot of:
(1) a biomarker or a combination of biomarkers selected from the group consisting of epidermal growth factor, transforming growth factor alpha and HER2 or;
(2) a combination of biomarkers comprising amphiregulin and one or more biomarkers selected from the group consisting of an epidermal growth factor, a transforming growth factor alpha, and HER2,
(b) determining the level of expression of a corresponding biomarker or biomarkers in an aliquot of the biological sample not contacted with the candidate agent,
(c) observing the effect of the candidate agent by comparing the level of expression of the biomarker or biomarkers in the aliquot of the biological sample contacted with the candidate agent and the level of expression of the corresponding biomarker or biomarkers in the aliquot of the biological sample not contacted with the candidate agent,
(d) identifying said agent from said observed effect, wherein an at least 10% difference between the level of expression of the biomarker or biomarkers in the aliquot of the biological sample contacted with the candidate agent and the level of expression of the corresponding biomarker or biomarkers in the aliquot of the biological sample not contacted with the candidate agent is an indication of an effect of the candidate agent.

Preferably, the candidate agent is a candidate inhibitory agent. Preferably, said candidate agent is a candidate enhancing agent.

In another embodiment of the invention, a candidate agent derived by the method according to the invention is provided.

In another embodiment of the invention, a pharmaceutical preparation comprising an agent according to the invention is provided.

In yet another embodiment of the invention, an agent according to the invention is used for the preparation of a composition for the treatment of cancer. Preferred forms of cancer are disclosed above.

In another preferred embodiment of the invention, a method of producing a drug comprising the steps of the method according to the invention and
  (i) synthesizing the candidate agent identified in step (c) above or an analog or derivative thereof in an amount sufficient to provide said drug in a therapeutically effective amount to a subject; and/or
  (ii) combining the drug candidate the candidate agent identified in step (c) above or an analog or derivative thereof with a pharmaceutically acceptable carrier.

In another embodiment of the invention, a marker protein or a marker polynucleotide selected from the group consisting of a amphiregulin, epidermal growth factor, transforming growth factor alpha and HER2 marker protein or marker polynucleotide is used for identifying a candidate agent or for selecting a composition for inhibiting the progression of a disease in a patient. The disease is preferably cancer and the patient is preferably a cancer patient as disclosed above.

In another embodiment of the invention, a HER inhibitor is used for the manufacture of a pharmaceutical composition for treating a human cancer patient characterized in that said treating or treatment includes assessing in a biological sample from the patient
  (a) a marker gene or a combination of marker genes selected from the group consisting of an epidermal growth factor, a transforming growth factor alpha and a HER2 marker gene or;
  (b) a combination of marker genes comprising an amphiregulin marker gene and a marker gene selected from the group consisting of an epidermal growth factor, a transforming growth factor alpha and a HER2 marker gene.

The manufacture of a pharmaceutical composition for treating a human cancer patient and particularly the formulation is described in WO 01/00245, incorporated herein by reference, particularly for the antibody 2C4.

In an preferred embodiment of the invention, in the use of the HER dimerization inhibitor for the manufacture of a pharmaceutical composition for treating a human cancer patient, the treatment includes assessing the marker gene or the combination of marker genes at least one time or repeatedly during treatment. Preferably, the level of expression of the marker gene or the level of expression of the combination of marker genes is assessed. Preferably, the HER inhibitor is an antibody, preferably the antibody 2C4. Preferably, the patient is a breast cancer, ovarian cancer, lung cancer or prostate cancer patient.

In all embodiments of the invention, combinations of the marker genes, marker polynucleotides or marker proteins are used as disclosed above. In all embodiments of the invention, preferred values for the difference of the level of expression determined in the respective steps are also as disclosed above.

The following examples, sequence listing and figures are provided to aid the understanding of the present invention, the true scope of which is set forth in the appended claims. It is understood that modifications can be made in the procedures set forth without departing from the spirit of the invention.

EXAMPLES

Statistical Methods

The statistical tasks comprise the following steps:
1. Pre-selection of candidate biomarkers
2. Pre-selection of relevant clinical prognostic covariates
3. Selection of biomarker prediction functions at an univariate level
4. Selection of biomarker prediction functions including clinical covariates at an univariate level
5. Selection of biomarker prediction functions at a multivariate level
6. Selection of biomarker prediction functions including clinical covariates at a multivariate level The following text details the different steps:

Ad1: Pre-selection of candidate biomarkers: The statistical pre-selection of candidate biomarkers is oriented towards the strength of association with measures of clinical benefit. For this purpose the different clinical endpoints may be transformed in derived surrogate scores, as e.g. an ordinal assignment of the degree of clinical benefit or morbidity scores regarding TTP or TTD which avoid censored observations. These surrogate transformed measures can be easily used for simple correlation analysis, e.g. by the non-parametric Spearman rank correlation approach. An alternative here is to use the biomarker measurements as metric covariates in Time-to-event regression models, as e.g. Cox proportional hazard regression. Depending on the statistical distribution of the biomarker values this step may require some pre-processing, as e.g. variance stabilizing transformations and the use of suitable scales or, alternatively, a standardization step like e.g. using percentiles instead of raw measurements. A further approach is inspection of bivariate scatter plots, e.g. by displaying the scatter of (x-axis=biomarker value, y-axis=measure of clinical benefit) on a single patient basis. Here also some non-parametric regression line as e.g. achieved by smoothing splines can be useful to visualize the association of biomarker and clinical benefit.

The goal of these different approaches is the pre-selection of biomarker candidates, which show some association with clinical benefit in at least one of the benefit measures employed, while results for other measures are not contradictory. When there are available control groups, then differences in association of biomarkers with clinical benefit in the different arms could be a sign of differential prediction which makes the biomarker eligible for further consideration.

Ad2: Pre-selection of relevant clinical prognostic covariates: The term "clinical covariate" here is used to describe all other information about the patient, which are in general available at baseline. These clinical covariates comprise demographic information like sex, age etc., other anamnestic information, concomitant diseases, concomitant therapies, result of physical examinations, common laboratory parameters obtained, known properties of the target tumor, information quantifying the extent of malignant disease, clinical performance scores like ECOG or Karnofsky index, clinical disease staging, timing and result of pretreatments and disease history as well as all similar information, which may be associated with the clinical prognosis. The statistical pre-selection of clinical covariates parallels the approaches for pre-selecting biomarkers and is as well oriented towards the strength of association with measures of clinical benefit. So in principle the same methods apply as considered under 1. In addition to statistical criteria, also criteria from clinical experience and theoretical knowledge may apply to pre-select relevant clinical covariates.

The prognosis by clinical covariates could interact with the prognosis of the biomarkers. They will be considered for refined prediction rules if necessary.

Ad3: Selection of biomarker prediction functions at an univariate level: The term "prediction function" will be used in a general sense to mean a numerical function of a biomarker measurement which results in a number which is scaled to imply the target prediction.

A simple example is the choice of the Heaviside function for a specific cutoff c and a biomarker measurement x, where the binary prediction A or B is to be made, then If $H(x-c)=0$ then predict $A$.

If $H(x-c)=1$ then predict $B$.

This is probably the most common way of using univariate biomarker measurements in prediction rules. The definition of a prediction function usually recurs to an existing training data set which can be used to explore the prediction possibilities. In order to achieve a suitable cutoff c from the training set different routes can be taken. First the scatterplot with smoothing spline mentioned under 1 can be used to define the cutoff. Alternatively some percentile of the distribution could be chosen, e.g. the median or a quartile. Cutoffs can also be systematically extracted by investigating all possible cutoffs according to their prediction potential with regard to the measures of clinical benefit. Then these results can be plotted to allow for an either manual selection or to employ some search algorithm for optimality. This was realized based on the endpoints TTP and TTD using a Cox model, where at each test cutoff the biomarker was used as a binary covariate. Prediction criteria were the resulting Hazard ratios. Then the results for TTP and TTD can be considered together in order to chose a cutoff which shows prediction in line with both endpoints Another uncommon approach for choosing a prediction function can be based on a fixed parameter Cox regression model obtained from the training set with biomarker values (possibly transformed) as covariate. Then the prediction could simply depend on whether the computed Hazard ratio is smaller or greater than 1.

A further possibility is to base the decision on some likelihood ratio (or monotonic transform of it), where the target probability densities were pre-determined in the training set for separation of the prediction states. Then the biomarker would be plugged into some function of the density ratios.

Ad4: Selection of biomarker prediction functions including clinical covariates at an univariate level: Univariate here refers to using only one biomarker—with regard to clinical covariates this can be a multivariate model. This approach parallels the search without clinical covariates, only that the methods should allow for incorporating the relevant covariate information. The scatterplot method of choosing a cutoff allows only a limited use of covariates, e.g. a binary covariate could be color coded within the plot. If the analysis relies on some regression approach then the use of covariates (also many of them at a time) is usually facilitated. The cutoff search based on the Cox model described under 3, allows for an easy incorporation of covariates and thereby leads to a covariate adjusted univariate cutoff search. The adjustment by covariates may be done as covariates in the model or via the inclusion in a stratified analysis.

Also the other choices of prediction functions allow for the incorporation of covariates.

This is straightforward for the Cox model choice as prediction function. There is the option to estimate the influence of covariates on an interaction level, which means that e.g. for different age groups different Hazard ratios apply.

For the likelihood ratio type of prediction functions, the prediction densities must be estimated including covariates. Here the methodology of multivariate pattern recognition can be used or the biomarker values can be adjusted by multiple regression on the covariates (prior to density estimation).

The CART technology (Classification And Regression Trees; Breiman L., Friedman J. H., Olshen R. A., Stone C. J., Chapman & Hall (Wadsworth, Inc.), New York, 1984) can be used for a biomarker (raw measurement level) plus clinical covariates employing a clinical benefit measure as response. This way cutoffs are searched and a decision tree type of functions will be found involving the covariates for prediction. The cutoffs and algorithms chosen by CART are frequently close to optimal and may be combined and unified by considering different clinical benefit measures.

Ad5: Selection of biomarker prediction functions at a multivariate level: When there are several biomarker candidates which maintain their prediction potential within the different univariate prediction function choices, then a further improvement may be achieved by combinations of biomarkers, i.e. considering multivariate prediction functions.

Based on the simple Heaviside function model combinations of biomarkers may be evaluated, e.g. by considering bivariate scatterplots of biomarker values where optimal cutoffs are indicated. Then a combination of biomarkers can be achieved by combining different Heaviside function by the logical AND and OR operators in order to achieve an improved prediction.

The CART technology (Classification And Regression Trees) can be used for multiple biomarkers (raw measurement level) and a clinical benefit measure as response, in order to achieve cutoffs for biomarkers and decision tree type of functions for prediction. The cutoffs and algorithms chosen by CART are frequently close to optimal and may be combined and unified by considering different clinical benefit measures.

The Cox-regression can be employed on different levels. A first way is to incorporate the multiple biomarkers in a binary way (i.e. based on Heaviside functions with some cutoffs). The other option is to employ biomarkers in a metric way (after suitable transformations), or a mixture of the binary and metric approach. The evolving multivariate prediction function is of the Cox type as described under 3.

The multivariate likelihood ratio approach is difficult to realize but presents as well as an option for multivariate prediction functions.

Ad6: Selection of biomarker prediction functions including clinical covariates at a multivariate level: When there are relevant clinical covariates then a further improvement may be achieved by combining multiple biomarkers with multiple clinical covariates. The different prediction function choices will be evaluated with respect to the possibilities to include clinical covariates.

Based on the simple logical combinations of Heaviside functions for the biomarkers, further covariates may be included to the prediction function based on logistic regression model obtained in the training set.

The CART technology and the evolving decision trees can be easily used with additional covariates, which would include these in the prediction algorithm.

All prediction functions based on the Cox-regression can use further clinical covariates. There is the option to estimate the influence of covariates on an interaction level, which means that e.g. for different age groups different Hazard ratios apply.

The multivariate likelihood ratio approach is not directly extendible to the use of additional covariates.

Example 1

Baseline Blood Sera from HER2 Low Expressing Metastatic Breast Cancer Patients Treated with Pertuzumab were Assessed for Levels of HER Ligands and Shedded HER2 (HER2 ECD), as Described Below Kits used for assessment of the serum biomarkers:

| Marker | Assay | Distribution |
| --- | --- | --- |
| HER2-ECD | Bayer HER-2/neu ELISA, Cat.#: EL501 | DakoCytomation N.V./S.A., Interleuvenlaan 12B, B-3001 Heverlee |
| Amphiregulin | DuoSet ELISA Development System Human Amphiregulin, Cat. #: DY262 | R&D Systems Ltd., 19 Barton Lane, Abingdon OX14 3NB, UK |
| EGF | Quantikine human EGF ELISA kit, Cat. #: DEG00 | R&D Systems Ltd., 19 Barton Lane, Abingdon OX14 3NB, UK |
| TGF-alpha | Quantikine ® Human TGF-alpha Immunoassay, Cat. #: DTGA00 | R&D Systems Ltd., 19 Barton Lane, Abingdon OX14 3NB, UK |

Protocols:

HER2-ECD:

HER2-ECD ELISA was performed according to the recommendations of the manufacturer.

Amphiregulin:

Prepare all reagents (provided with the kit), standard dilutions (provided with the kit) and samples Provide EvenCoat Goat Anti-mouse IgG microplate strips (R&D, Cat. # CP002; not provided with the kit) in the frame. The frame is now termed ELISA plate.

Determine of the required number of wells (number of standard dilutions+number of samples).

Determine the plate layout.

Add 100 µl diluted capture antibody (provided with the kit; 1:180 in PBS) to each well.

Incubate at r.t. for 1 hour.

Aspirate each well and wash, repeating the process three times for a total of four washes. Wash by filling each well with 400 µl Wash buffer (not provided with the kit; 0.05% Tween-20 in PBS was used), using a manifold dispenser, and subsequent aspiration. After the last wash, remove any remaining Wash buffer by aspirating. Invert the plate and blot it against clean paper towels.

Add 100 µl standard dilution or diluted sample (see below) per well. Change tip after every pipetting step.

Cover plate with the adhesive strip (provided with the kit).

Incubate for 2 hours at r.t. on a rocking platform.

Repeat the aspiration/wash as described previously.

Aspirated samples and wash solutions are treated with laboratory disinfectant.

Add 100 µl Detection Antibody (provided with the kit) diluted 1:180 in Reagent diluent (not provided with the kit; 1% BSA (Roth; Albumin Fraction V, Cat. # T844.2) in PBS was used) per well Incubate for 2 hours at r.t.

Repeat the aspiration/wash as described previously.

Add 100 µl working dilution of the Streptavidin-HRP to each well (provided with the kit; 1:200 dilution in Reagent diluent). Cover with a new adhesive strip.

Incubate for 20 min at r.t.

Repeat the aspiration/wash as described previously.

Add 100 µl Substrate Solution (R&D, Cat. # DY999; not provided with the kit) to each well.

Incubate for 20 min at r.t. Protect from light.

Add 50 µl Stop Solution (1.5 M H2SO4 (Schwefelsäure reinst, Merck, Cat. # 713); not provided with the kit) to each well. Mix carefully.

Determine the optical density of each well immediately, using a microplate reader set to 450 nm.

Amphiregulin Standard Curve:

A 40 ng/ml amphiregulin stock solution was prepared in 1% BSA in PBS, aliquotted and stored at −80° C. Amphiregulin solutions in 20% BSA in PBS were not stable beyond 2 weeks and were therefore not used. From the aliquotted amphiregulin stock solution, the amphiregulin standard curve was prepared freshly in 20% BSA in PBS prior to each experiment. The highest concentration was 1000 pg/ml (1:40 dilution of the amphiregulin stock solution). The standards provided with the ELISA kit produced a linear standard curve. Excel-based analysis of the curves allowed the determination of curve equations for every ELISA.

Amphiregulin Samples:

When samples were diluted 1:1 in Reagent Diluent, all samples were within the linear range of the ELISA. Each sample was measured in duplicates. Dependent on the quality of the data, and on sufficient amounts of serum, determinations were repeated in subsequent experiments if necessary.

EGF:

Prepare all reagents (provided with the kit), standard dilutions (provided with the kit) and samples Remove excess antibody-coated microtiter plate strips (provided with the kit) from the frame. The frame is now termed ELISA plate.

Determine of the required number of wells: (Number of standard dilutions+number of samples)×2

Determine the plate layout.

Add 50 µl Assay Diluent RD1 (provided with the kit) to each well

Add 200 µl standard dilution or diluted sample (e.g. 1:20 in Calibrator Diluent RD6H) per well. Change tip after every pipetting step.

Cover plate with the adhesive strip (provided with the kit).

Incubate for 2 hours at r.t. on a rocking platform.

Aspirate each well and wash, repeating the process three times for a total of four washes.

Wash by filling each well with 400 µl Wash Buffer (provided with the kit), using a manifold dispenser, and subsequent aspiration. After the last wash, remove any remaining Wash buffer by aspirating. Invert the plate and blot it against clean paper towels.

Aspirated samples and wash solutions are treated with laboratory disinfectant. Add 200 μl of Conjugate (provided with the kit) to each well. Cover with a new adhesive strip.

Incubate for 2 hours at r.t.

Repeat the aspiration/wash as described previously.

Add 200 μl Substrate Solution (provided with the kit) to each well.

Incubate for 20 min at r.t. Protect from light.

Add 50 μl Stop Solution (provided with the kit) to each well. Mix carefully.

Determine the optical density of each well within 30 minutes, using a microplate reader set to 450 nm.

EGF Standard Curve:

The standards provided with the ELISA kit produced a linear standard curve. Also very small concentrations showed detectable results.

EGF Samples:

A total of four assays with the samples was performed. Each sample was measured 2-5 times, the number of determinations being dependent on the quality of the results (mean+/−SD) and the availability of sufficient amounts of serum. When samples were diluted 1:20 in Calibrator Diluent RD6H, all samples were within the linear range of the ELISA.

TGF-alpha:

Prepare all reagents (provided with the kit), standard dilutions (provided with the kit) and samples Remove excess antibody-coated microtiter plate strips (provided with the kit) from the frame. The frame is now termed ELISA plate.

Determine of the required number of wells: (Number of standard dilutions+number of samples)×2

Determine the plate layout.

Add 100 μl Assay Diluent RD1W (provided with the kit) to each well

Add 50 μl standard dilution or sample per well. Change tip after every pipetting step.

Cover plate with the adhesive strip (provided with the kit).

Incubate for 2 hours at r.t. on a rocking platform.

Aspirate each well and wash, repeating the process three times for a total of four washes. Wash by filling each well with 400 μl Wash Buffer (provided with the kit), using a manifold dispenser, and subsequent aspiration. After the last wash, remove any remaining Wash buffer by aspirating. Invert the plate and blot it against clean paper towels.

Aspirated samples and wash solutions are treated with laboratory disinfectant.

Add 200 μl of TGF-alpha Conjugate (provided with the kit) to each well. Cover with a new adhesive strip.

Incubate for 2 hours at r.t.

Repeat the aspiration/wash as described previously.

Add 200 μl Substrate Solution (provided with the kit) to each well.

Incubate for 30 min at r.t. Protect from light.

Add 50 μl Stop Solution (provided with the kit) to each well. Mix carefully.

Determine the optical density of each well within 30 minutes, using a microplate reader set to 450 nm.

TGF-alpha Standard Curve:

The standards provided with the ELISA kit produced a linear standard curve. Also very small concentrations showed detectable results.

TGF-alpha Samples:

A total of four assays with the samples was performed. Samples were measured in 2-4 independent assays.

Figure 2:
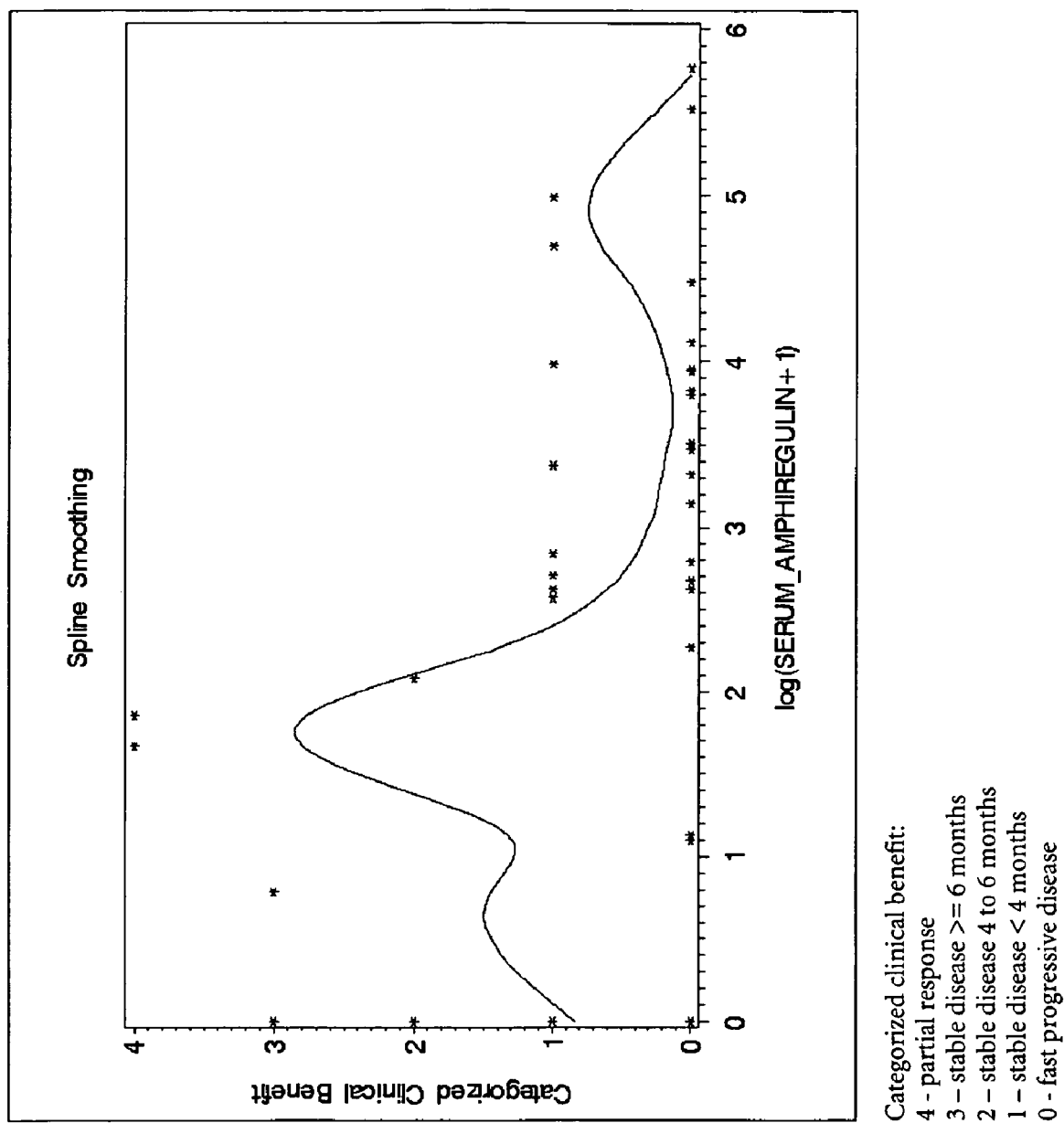
FIG. 2: Scatterplot Amphiregulin logarithmic transformation versus categorized clinical benefit

The serum data was analyzed to identify factors the baseline serum levels of which would be associated with response to the Pertuzumab treatment. For all factors a skewed pattern of the distribution (mean, standard deviation, median, minimum, maximum) was observed. A monotonic transform was used to reduce the skewness based on the logarithm: Log(x+1). In a univariate analysis, it was explored whether suitable cut-points for the factors could be defined which would relate to the probability of response (in this example defined as clinical benefit). Here, patients with clinical benefit were defined as those who achieved a partial response (PR) or maintained stable disease for at least 6 months. Scatterplots of the factors versus the response categories were investigated. FIG. 1 and FIG. 2 show a plotting of the clinical response categories versus the logarithmic transformation of the serum levels of TGF-alpha and amphiregulin, respectively, to exemplify the approach.

Based on the scatterplots, cut-points were selected for the factors to define groups of patients, who have experienced greater clinical benefit. FIG. 3 (TGF-alpha), FIG. 4 (Amphiregulin), FIG. 5 (EGF), and FIG. 6 (HER2-ECD) show the clinical benefit in relation to the different factor groupings based on the exploratory cut-points calculated to the original factor units. The cut-points separate out some of the patients without clinical benefit, and hence, elevate the response rate for the group with greater clinical benefit.

Example 2

In this example the exploratory cut-points from Example 1 were used to assess the univariate effect of the factor groupings on different measures of the clinical benefit of the Pertuzumab treatment, using time to progression/or death (TTP) and time to death (TTD) as alternative clinical endpoints. Significant effects were observed for TGF-alpha, Amphiregulin, EGF and HER2-ECD in Kaplan-Meier estimates and log-rank tests for TTP and/or TTD, as shown in an overview in FIG. 7.

Figure 8:
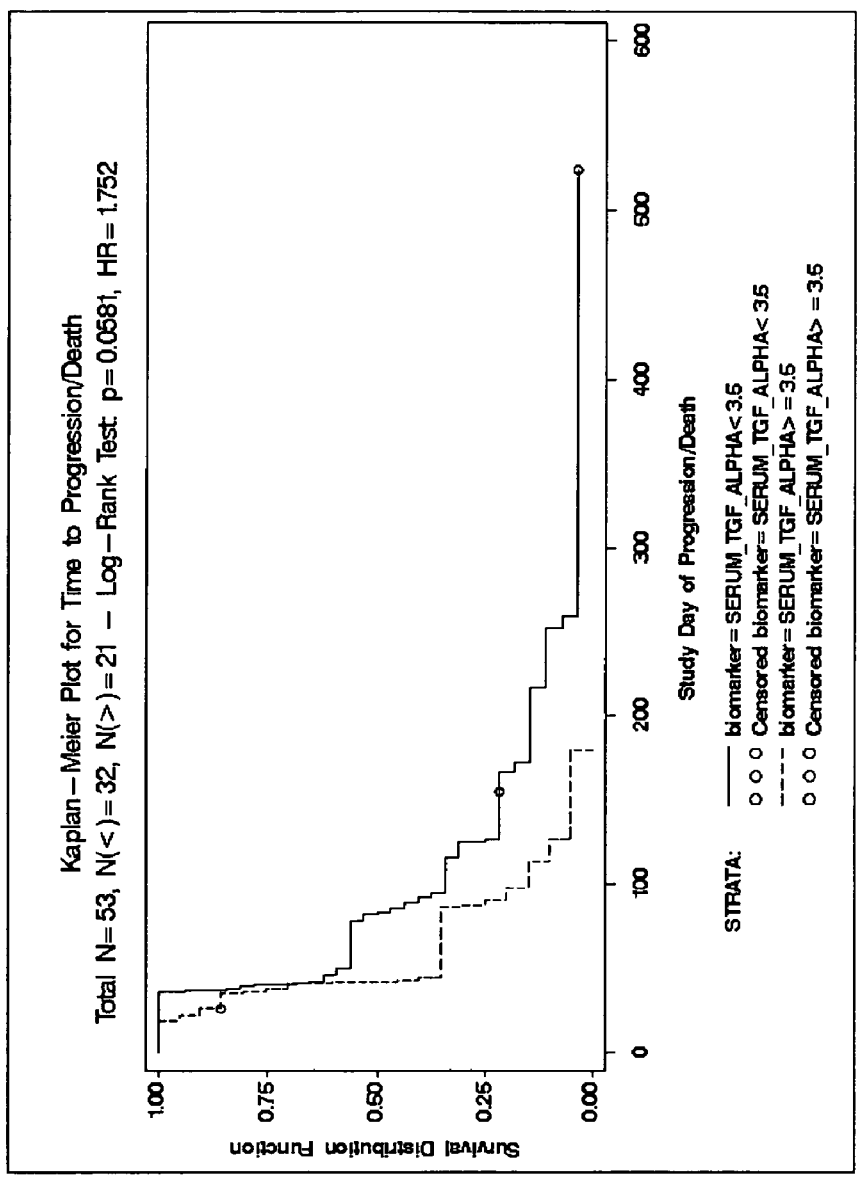
FIG. 8: TGF-alpha Kaplan Meier plot for time to progression/death based on exploratory single marker cut-point
Figure 9:
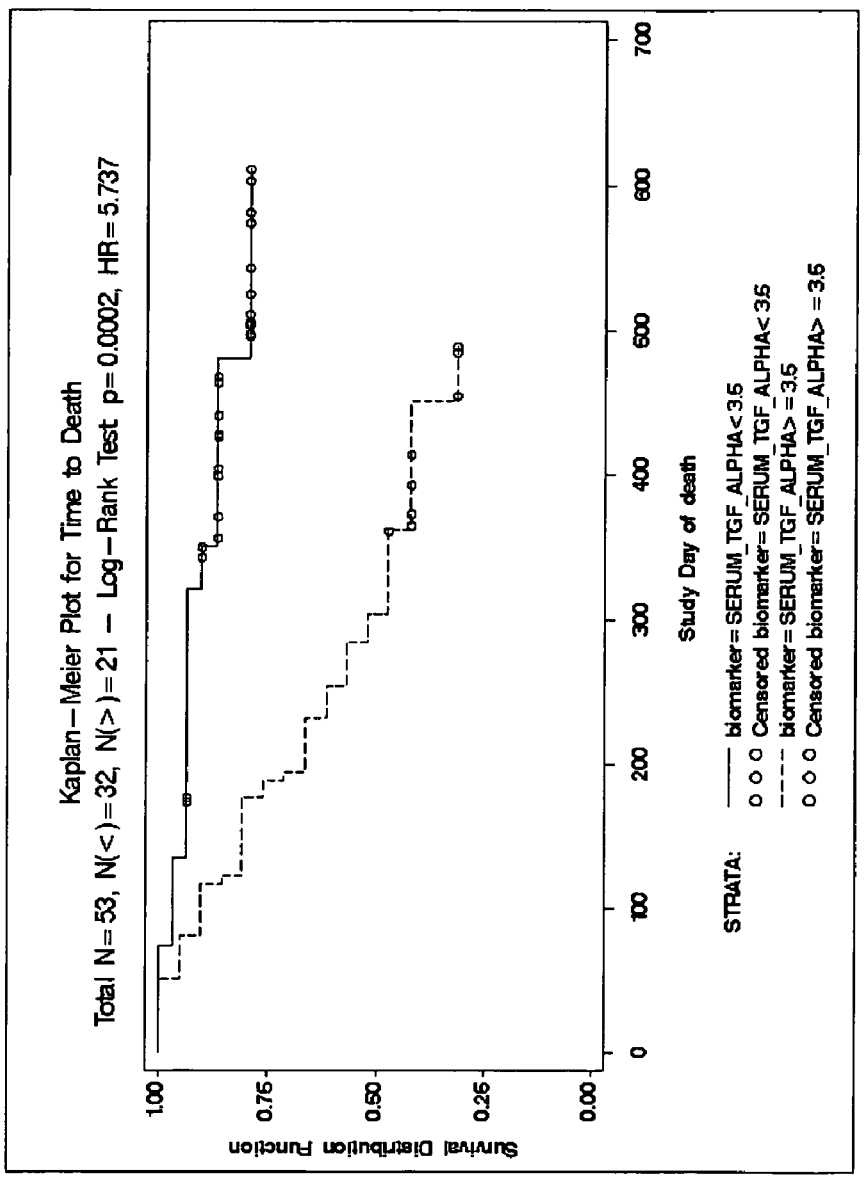
FIG. 9: TGF-alpha Kaplan Meier plot for time to death based on exploratory single marker cut-point
Figure 10:
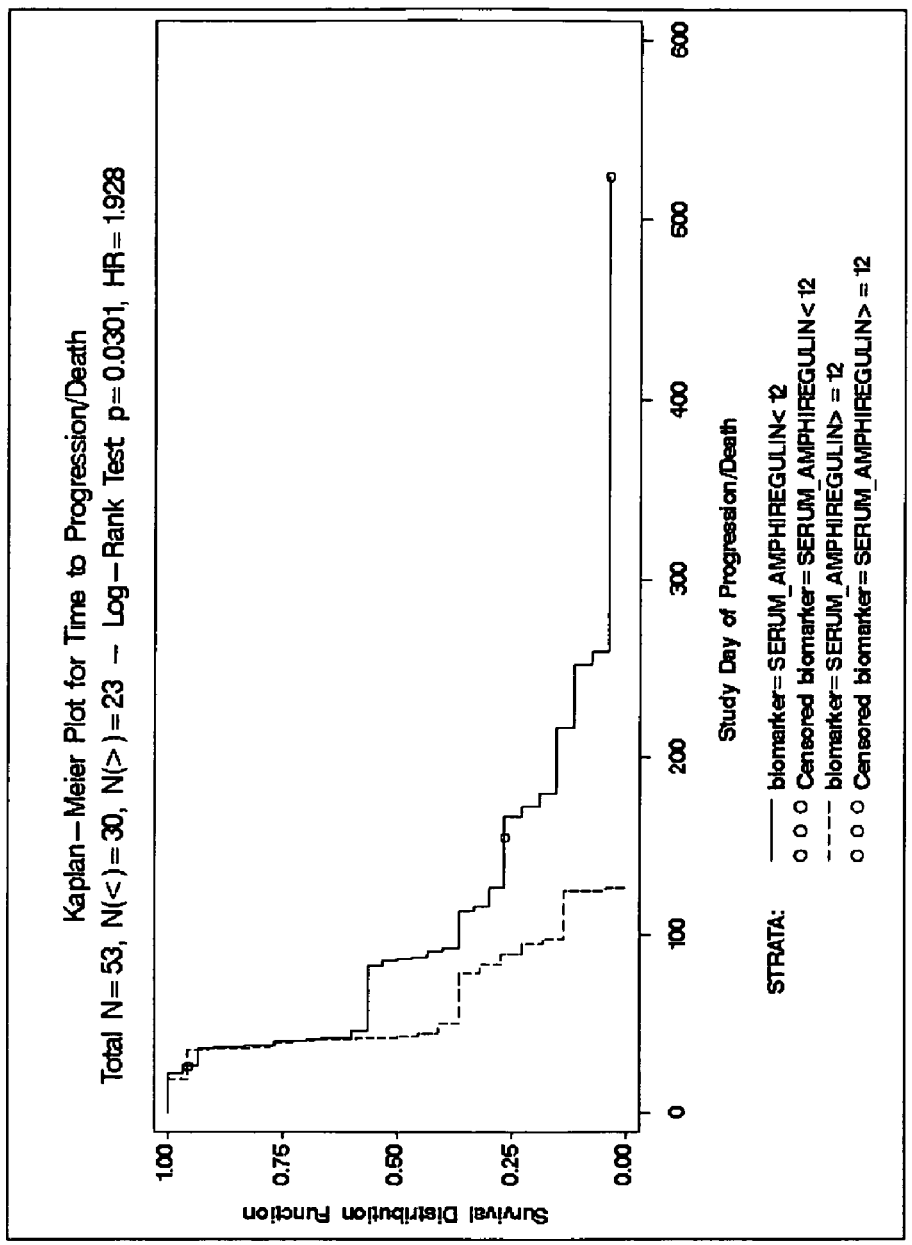
FIG. 10: Amphiregulin Kaplan Meier plot for time to progression/death based on exploratory single marker cut-point
Figure 11:
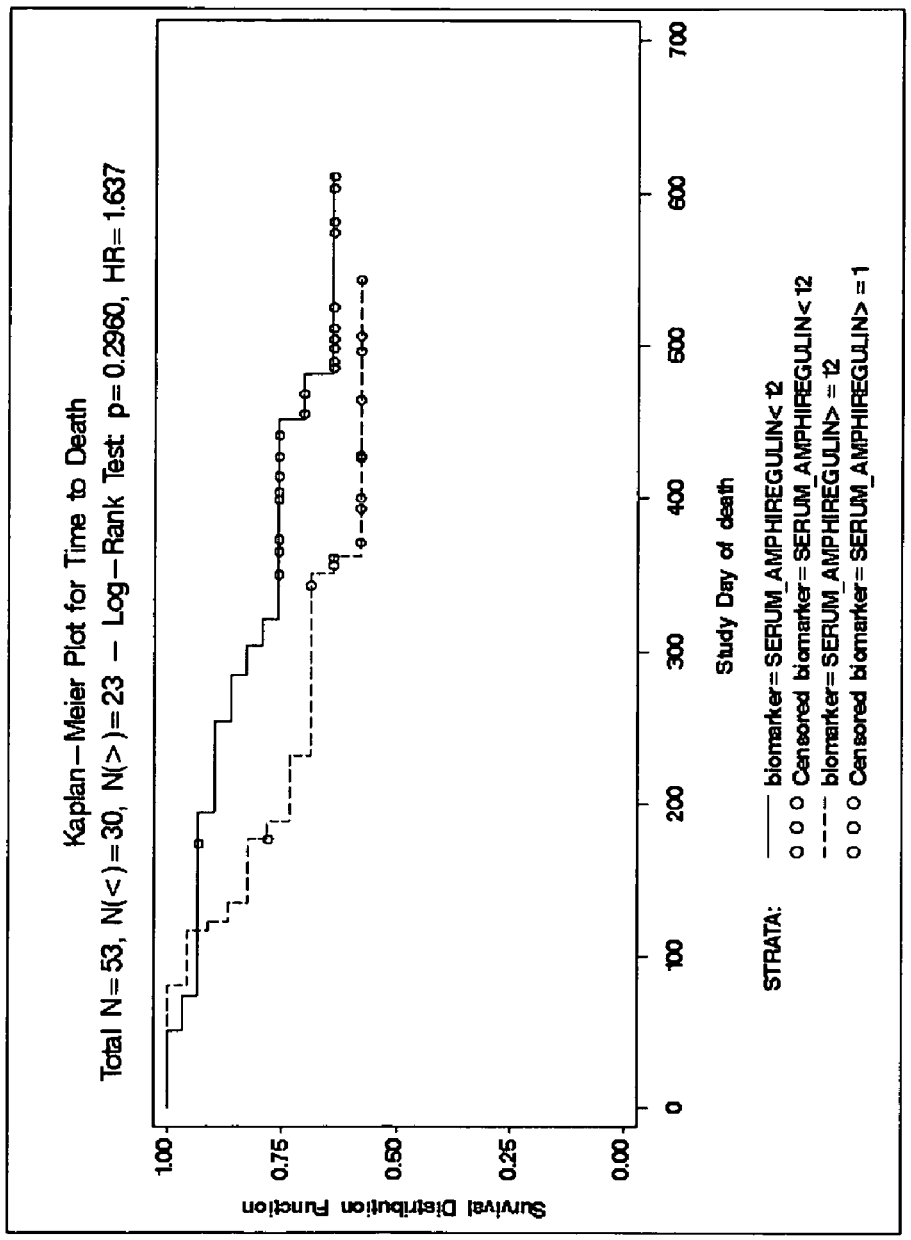
FIG. 11: Amphiregulin Kaplan Meier plot for time to death based on exploratory single marker cut-point
Figure 12:
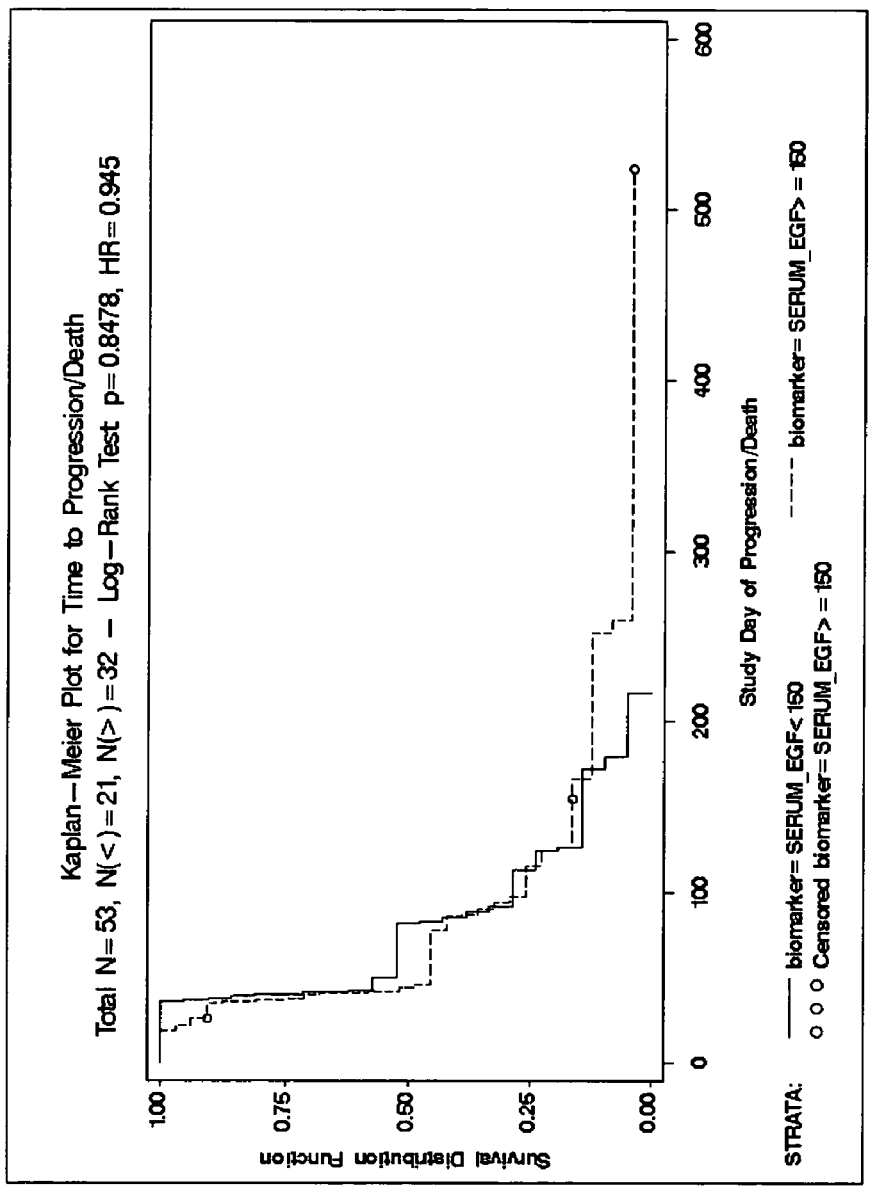
FIG. 12: EGF Kaplan Meier plot for time to progression/death based on exploratory single marker cut-point
Figure 13:
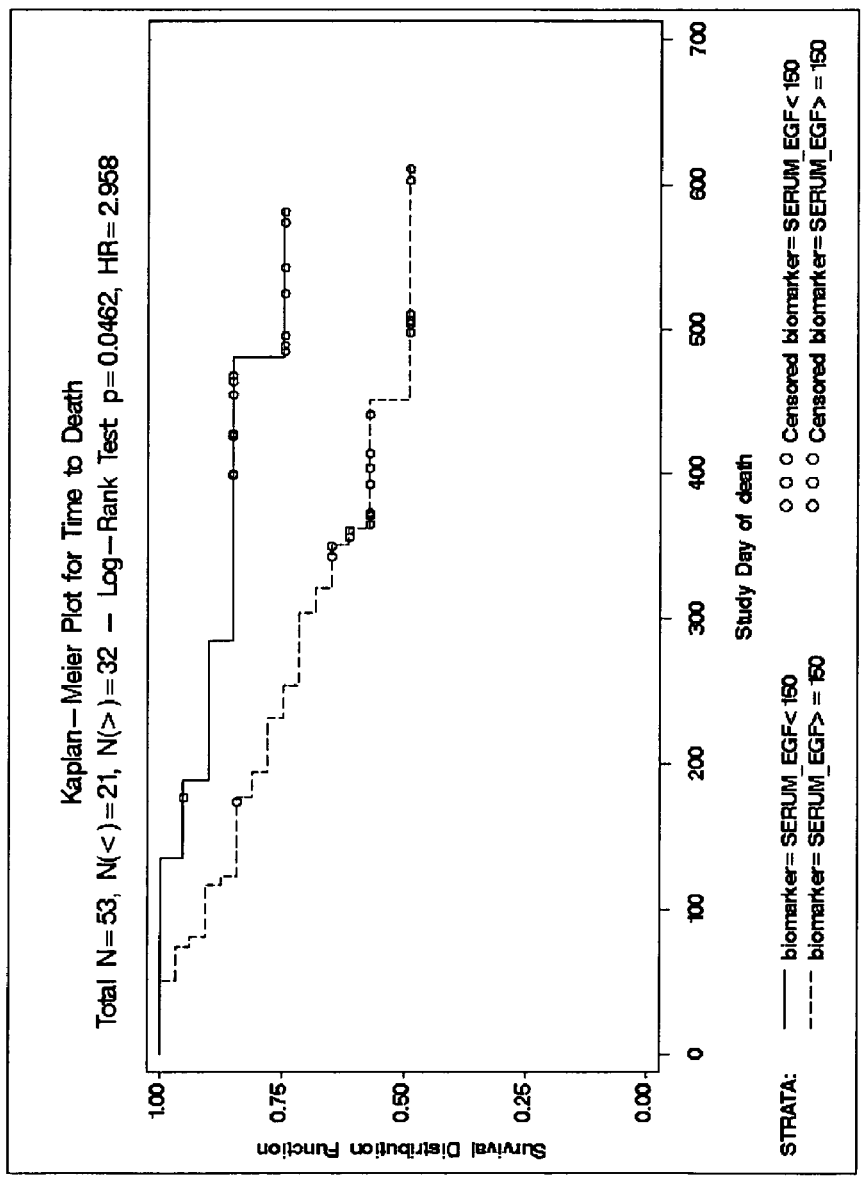
FIG. 13: EGF Kaplan Meier plot for time to death based on exploratory single marker cut-point
Figure 14:
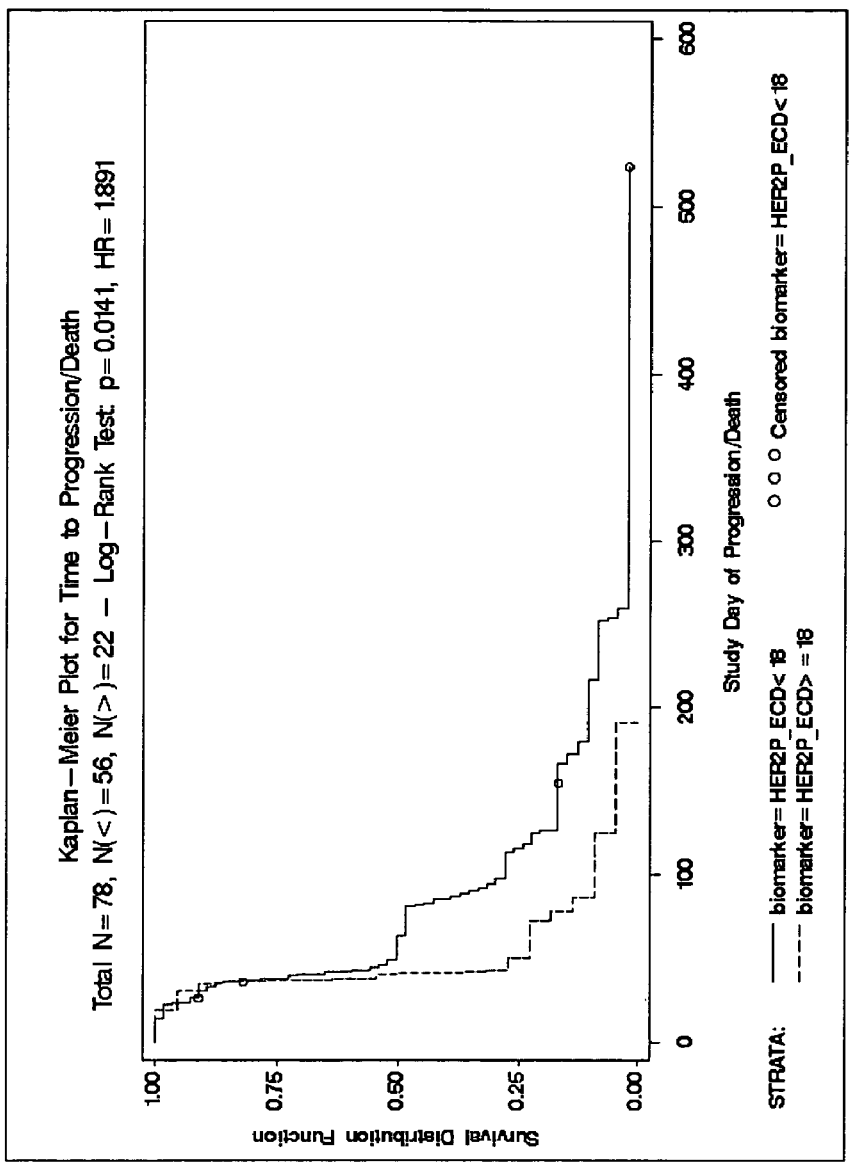
FIG. 14: HER2-ECD Kaplan Meier plot for time to progression/death based on exploratory single marker cut-point
Figure 15:
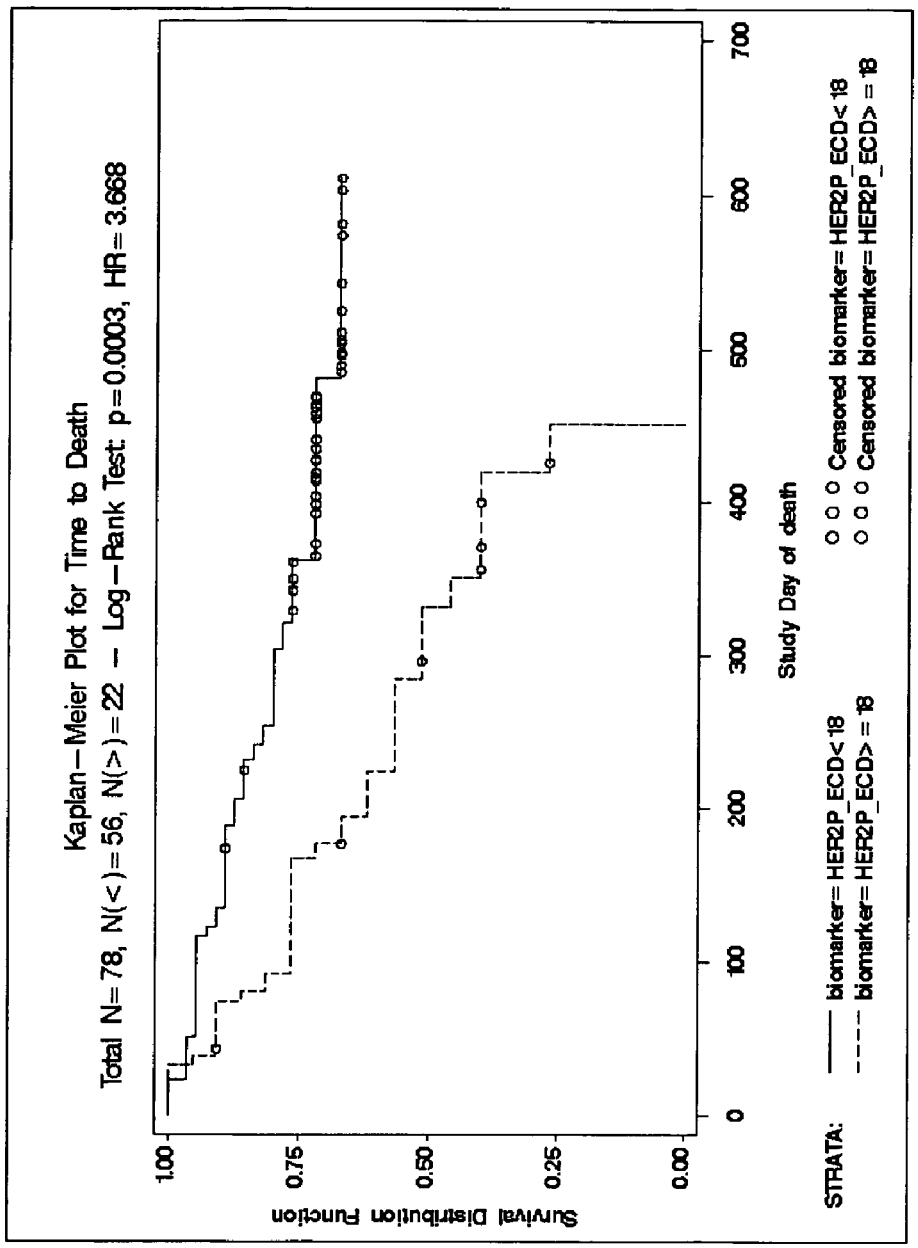
FIG. 15: HER2-ECD Kaplan Meier plot for time to death based on exploratory single marker cut-point

The Kaplan-Meier plots displaying the hazard ratio are given for TTP and TTD (highest number of events observed) in FIG. 8 and FIG. 9 (TGF-alpha), 10 and 11 (Amphiregulin), 12 and 13 (EGF), and 14 and 15 (HER2-ECD), showing the pronounced effect of a grouping based on these factors on the clinical outcome of the patients treated with Pertuzumab.

Example 3

Figure 18:
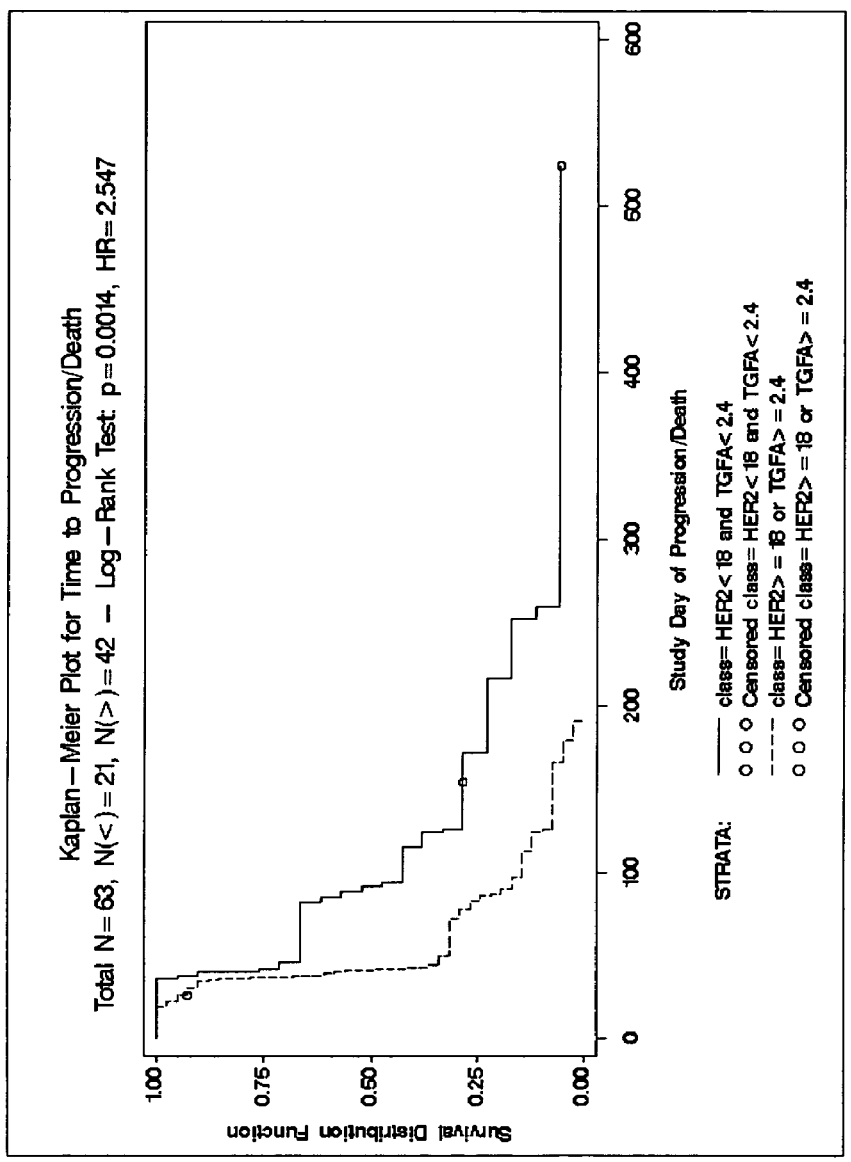
FIG. 18: HER2-ECD/TGF-alpha Kaplan Meier plot for time to progression/death based on exploratory combination marker cut-point
Figure 19:
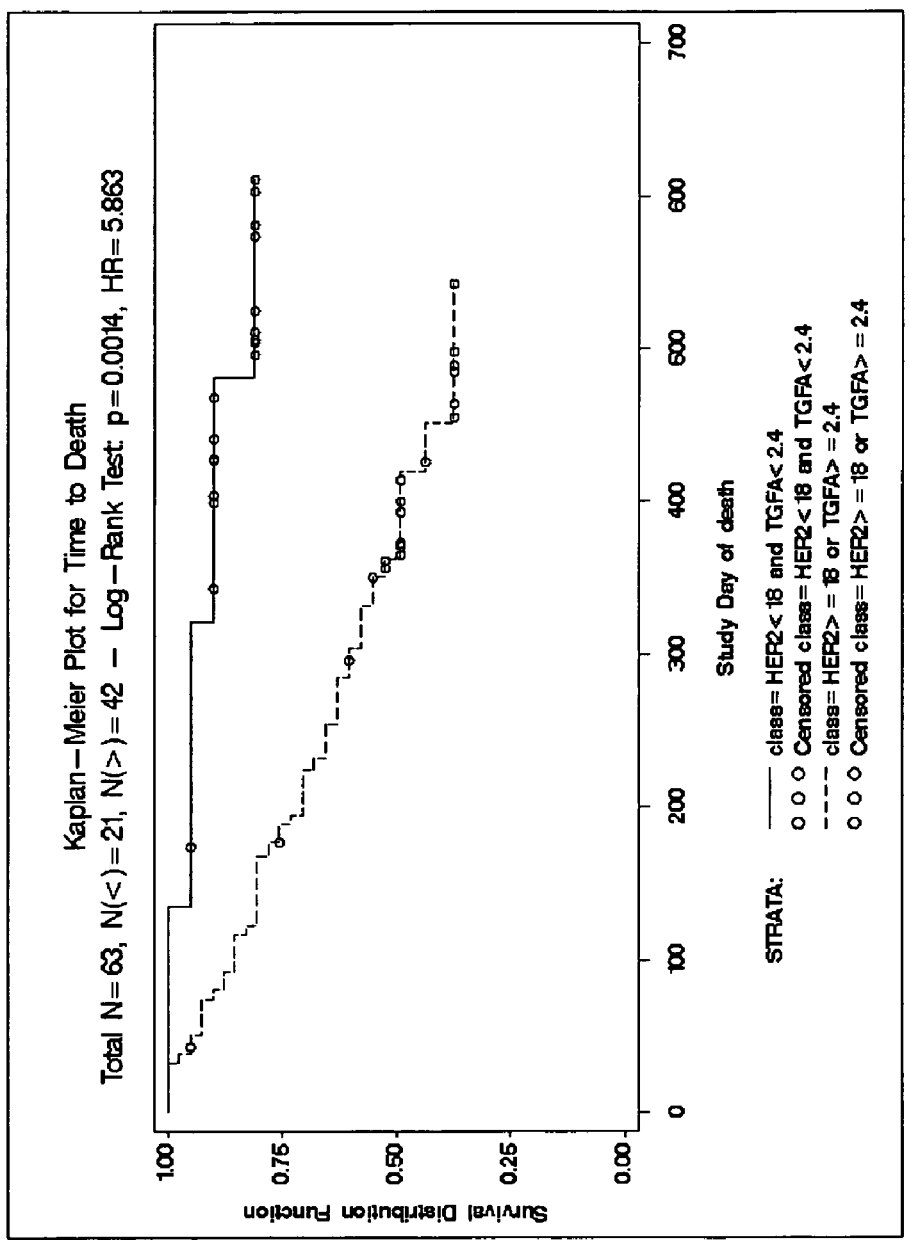
FIG. 19: HER2-ECD/TGF-alpha Kaplan Meier plot for time to death based on exploratory combination marker cutpoint

In this example multivariate approaches were used to identify combinations of factors that would further improve the identification of patients with greater benefit from the Pertuzumab treatment. Results, as derived from a CART approach (Classification And Regression Trees), are reflected. The CART classification approach made it necessary to specify as the benefit group all values in clinical benefit above of 0. As variables serum levels of HER2-ECD, TGF-alpha, Amphiregulin, and EGF were employed. A combination of serum HER2-ECD and serum TGF-alpha levels were selected to give best results. From the CART results optimized cut-points for a combination of serum HER2-ECD and serum TGF-alpha levels were derived, resulting in a rule for exploratory categorization of clinical benefit in the study population—a combination of low serum HER2-ECD values and low serum TGF-alpha values capturing 2/2 PR and 2/3 SD>6 months in the study population and excluding a reasonable number of fast progressing patients. FIG. 16 shows the clinical benefit in relation to the TGF-alpha/HER2-ECD combination groupings based on the exploratory combination cut-point. FIG. 17 summarizes the effect of a combination of TGF-alpha and HER2-ECD on TTP and TTD. The Kaplan-Meier estimates and the hazard ratios given in FIG. 18 (TTP) and FIG. 19 (TTD) demonstrate the significant effect of the grouping based on a combination of these factors for on the clinical outcome of the patients treated with Pertuzumab.

Unless stated to the contrary, all compounds in the examples were prepared and characterized as described. All ranges recited herein encompass all combinations and subcombinations included within that range limit. All patents and publications cited herein are hereby incorporated by reference in their entirety for any purpose.

The invention claimed is:

1. A method of predicting the response of a metastatic breast cancer patient to treatment with pertuzumab comprising the steps of:
   (a) determining the amount of each of the following biomarkers in a biological sample from a metastatic breast cancer patient that has been treated with pertuzumab:
      (1) the amino acid sequence of SEQ ID NO: 1;
      (2) the amino acid sequence of SEQ ID NO: 2;
      (3) the amino acid sequence of SEQ ID NO: 3; and
      (4) the amino acid sequence consisting of residues 22 to 645 of SEQ ID NO: 4;
   (b) determining whether the amount assessed in step (a) is above or below a quantity that is associated with an increased or decreased clinical benefit to a metastatic breast cancer patient; and
   (c) predicting the response to the treatment with pertuzumab in the patient by evaluating the results of step (b).

2. The method of claim 1 wherein said biological sample is obtained from blood serum and the quantity of the amino acid sequence of SEQ ID NO: 3 that is associated with an increased clinical benefit to a metastatic breast cancer patient is between 2.0-10.0 pg/ml.

3. The method of claim 1 wherein said biological sample is obtained from blood serum and the quantity of the amino acid sequence consisting of residues 22 to 645 of SEQ ID NO: 4 that is associated with an increased clinical benefit to a metastatic breast cancer patient is between 12-22 ng/ml.

4. The method of claim 1 wherein said biological sample is obtained from blood serum and the quantity of the amino acid sequence of SEQ ID NO: 1 that is associated with an increased clinical benefit to a metastatic breast cancer patient is between 6-15 pg/ml.

5. The method of claim 1 wherein said biological sample is obtained from blood serum and the quantity of the amino acid sequence of SEQ ID NO: 2 that is associated with an increased clinical benefit to a metastatic breast cancer patient is between 100-250 pg/ml.

6. The method of claim 1 wherein said biological sample is obtained from blood serum and the quantity of said amino acid sequence consisting of residues 22 to 645 of SEQ ID NO: 4 that is associated with an increased clinical benefit to a patient is about 18 ng/ml and the quantity of said amino acid sequence of SEQ ID NO: 3 that is associated with an increased clinical benefit to a patient is about 3.5 pg/ml.

7. The method according to claim 1 wherein the quantity in step (b) of claim 1 is determined by:
   (1) determining the amount of said biomarkers in a plurality of biological samples from patients before treatment with pertuzumab,
   (2) treating the patients with pertuzumab,
   (3) determining the clinical benefit of each patient; and
   (4) correlating the clinical benefit of the patients treated with the pertuzumab to the amount of said biomarkers.

8. The method according to claim 1, wherein the amount of each biomarker is determined by using a reagent which specifically binds with said biomarker protein.

9. The method of claim 8, wherein the reagent is an antibody.

10. The method according to claim 1 wherein said biological sample is obtained from blood serum and the quantity of said amino acid sequence consisting of residues 22 to 645 of SEQ ID NO: 4 that is associated with an increased clinical benefit to a metastatic breast cancer patient is about 18 ng/ml.

11. A method of predicting the response of a metastatic breast cancer patient to treatment with pertuzumab comprising the steps of:
   (a) determining the amount of each of the following biomarkers in a biological sample from a metastatic breast cancer patient that has been treated with pertuzumab:
      (1) the amino acid sequence of SEQ ID NO: 1;
      (2) the amino acid sequence of SEQ ID NO: 2;
      (3) the amino acid sequence of SEQ ID NO: 3; and
      (4) the amino acid sequence consisting of residues 22 to 645 of SEQ ID NO: 4;
   (b) determining whether the amount assessed in step (a) of SEQ ID NO: 1 is between 6 and 15 pg/ml, of SEQ ID NO: 2 is between 100 and 250 pg/ml, of SEQ ID NO: 3 is between 2.0 and 10.0 pg/ml, and of the amino acid sequence consisting of residues 22 to 645 SEQ ID NO: 4 is between 12 and 22 ng/ml;
   (c) predicting the response to the treatment with pertuzumab in the patient by evaluating the results of step (b).

* * * * *

SEQUENCE LISTING

```
<160> NUMBER OF SEQ ID NOS: 14

<210> SEQ ID NO 1
<211> LENGTH: 252
<212> TYPE: PRT
<213> ORGANISM: Homo sapiens

<400> SEQUENCE: 1

Met Arg Ala Pro Leu Leu Pro Pro Ala Pro Val Val Leu Ser Leu Leu
 1               5                  10                  15

Ile Leu Gly Ser Gly His Tyr Ala Ala Gly Leu Asp Leu Asn Asp Thr
            20                  25                  30

Tyr Ser Gly Lys Arg Glu Pro Phe Ser Gly Asp His Ser Ala Asp Gly
        35                  40                  45

Phe Glu Val Thr Ser Arg Ser Glu Met Ser Ser Gly Ser Glu Ile Ser
    50                  55                  60

Pro Val Ser Glu Met Pro Ser Ser Glu Pro Ser Ser Gly Ala Asp
 65                 70                  75                  80

Tyr Asp Tyr Ser Glu Glu Tyr Asp Asn Glu Pro Gln Ile Pro Gly Tyr
                85                  90                  95

Ile Val Asp Asp Ser Val Arg Val Glu Gln Val Val Lys Pro Pro Gln
            100                 105                 110

Asn Lys Thr Glu Ser Glu Asn Thr Ser Asp Lys Pro Lys Arg Lys Lys
        115                 120                 125

Lys Gly Gly Lys Asn Gly Lys Asn Arg Arg Asn Arg Lys Lys Lys Asn
    130                 135                 140

Pro Cys Asn Ala Glu Phe Gln Asn Phe Cys Ile His Gly Glu Cys Lys
145                 150                 155                 160

Tyr Ile Glu His Leu Glu Ala Val Thr Cys Lys Cys Gln Gln Glu Tyr
                165                 170                 175

Phe Gly Glu Arg Cys Gly Glu Lys Ser Met Lys Thr His Ser Met Ile
            180                 185                 190

Asp Ser Ser Leu Ser Lys Ile Ala Leu Ala Ala Ile Ala Ala Phe Met
        195                 200                 205

Ser Ala Val Ile Leu Thr Ala Val Ala Val Ile Thr Val Gln Leu Arg
    210                 215                 220

Arg Gln Tyr Val Arg Lys Tyr Glu Gly Glu Ala Glu Glu Arg Lys Lys
225                 230                 235                 240

Leu Arg Gln Glu Asn Gly Asn Val His Ala Ile Ala
                245                 250

<210> SEQ ID NO 2
<211> LENGTH: 1207
<212> TYPE: PRT
<213> ORGANISM: Homo sapiens

<400> SEQUENCE: 2
```

-continued

```
Met Leu Leu Thr Leu Ile Ile Leu Leu Pro Val Val Ser Lys Phe Ser
 1               5                   10                  15

Phe Val Ser Leu Ser Ala Pro Gln His Trp Ser Cys Pro Glu Gly Thr
             20                  25                  30

Leu Ala Gly Asn Gly Asn Ser Thr Cys Val Gly Pro Ala Pro Phe Leu
         35                  40                  45

Ile Phe Ser His Gly Asn Ser Ile Phe Arg Ile Asp Thr Glu Gly Thr
     50                  55                  60

Asn Tyr Glu Gln Leu Val Val Asp Ala Gly Val Ser Val Ile Met Asp
 65                  70                  75                  80

Phe His Tyr Asn Glu Lys Arg Ile Tyr Trp Val Asp Leu Glu Arg Gln
                 85                  90                  95

Leu Leu Gln Arg Val Phe Leu Asn Gly Ser Arg Gln Glu Arg Val Cys
             100                 105                 110

Asn Ile Glu Lys Asn Val Ser Gly Met Ala Ile Asn Trp Ile Asn Glu
         115                 120                 125

Glu Val Ile Trp Ser Asn Gln Gln Glu Gly Ile Ile Thr Val Thr Asp
    130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
            180                 185                 190

Lys Ala Leu Leu Glu Thr Ser Glu Lys Ile Thr Ala Val Ser Leu Asp
        195                 200                 205

Val Leu Asp Lys Arg Leu Phe Trp Ile Gln Tyr Asn Arg Glu Gly Ser
    210                 215                 220

Asn Ser Leu Ile Cys Ser Cys Asp Tyr Asp Gly Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala
            260                 265                 270

Asn Lys His Thr Gly Lys Asp Met Val Arg Ile Asn Leu His Ser Ser
        275                 280                 285

Phe Val Pro Leu Gly Glu Leu Lys Val Val His Pro Leu Ala Gln Pro
    290                 295                 300

Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser
                325                 330                 335

His Leu Cys Met Cys Ala Glu Gly Tyr Ala Leu Ser Arg Asp Arg Lys
            340                 345                 350

Tyr Cys Glu Asp Val Asn Glu Cys Ala Phe Trp Asn His Gly Cys Thr
        355                 360                 365

Leu Gly Cys Lys Asn Thr Pro Gly Ser Tyr Tyr Cys Thr Cys Pro Val
    370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415
```

```
Glu Gly Pro Leu Cys Phe Cys Pro Glu Gly Ser Val Leu Glu Arg Asp
                420                 425                 430

Gly Lys Thr Cys Ser Gly Cys Ser Ser Pro Asp Asn Gly Gly Cys Ser
            435                 440                 445

Gln Leu Cys Val Pro Leu Ser Pro Val Ser Trp Glu Cys Asp Cys Phe
    450                 455                 460

Pro Gly Tyr Asp Leu Gln Leu Asp Glu Lys Ser Cys Ala Ala Ser Gly
465                 470                 475                 480

Pro Gln Pro Phe Leu Leu Phe Ala Asn Ser Gln Asp Ile Arg His Met
                485                 490                 495

His Phe Asp Gly Thr Asp Tyr Gly Thr Leu Leu Ser Gln Gln Met Gly
            500                 505                 510

Met Val Tyr Ala Leu Asp His Asp Pro Val Glu Asn Lys Ile Tyr Phe
    515                 520                 525

Ala His Thr Ala Leu Lys Trp Ile Glu Arg Ala Asn Met Asp Gly Ser
    530                 535                 540

Gln Arg Glu Arg Leu Ile Glu Glu Gly Val Asp Val Pro Glu Gly Leu
545                 550                 555                 560

Ala Val Asp Trp Ile Gly Arg Arg Phe Tyr Trp Thr Asp Arg Gly Lys
                565                 570                 575

Ser Leu Ile Gly Arg Ser Asp Leu Asn Gly Lys Arg Ser Lys Ile Ile
            580                 585                 590

Thr Lys Glu Asn Ile Ser Gln Pro Arg Gly Ile Ala Val His Pro Met
            595                 600                 605

Ala Lys Arg Leu Phe Trp Thr Asp Thr Gly Ile Asn Pro Arg Ile Glu
    610                 615                 620

Ser Ser Ser Leu Gln Gly Leu Gly Arg Leu Val Ile Ala Ser Ser Asp
625                 630                 635                 640

Leu Ile Trp Pro Ser Gly Ile Thr Ile Asp Phe Leu Thr Asp Lys Leu
                645                 650                 655

Tyr Trp Cys Asp Ala Lys Gln Ser Val Ile Glu Met Ala Asn Leu Asp
            660                 665                 670

Gly Ser Lys Arg Arg Arg Leu Thr Gln Asn Asp Val Gly His Pro Phe
            675                 680                 685

Ala Val Ala Val Phe Glu Asp Tyr Val Trp Phe Ser Asp Trp Ala Met
    690                 695                 700

Pro Ser Val Ile Arg Val Asn Lys Arg Thr Gly Lys Asp Arg Val Arg
705                 710                 715                 720

Leu Gln Gly Ser Met Leu Lys Pro Ser Ser Leu Val Val Val His Pro
                725                 730                 735

Leu Ala Lys Pro Gly Ala Asp Pro Cys Leu Tyr Gln Asn Gly Gly Cys
            740                 745                 750

Glu His Ile Cys Lys Lys Arg Leu Gly Thr Ala Trp Cys Ser Cys Arg
            755                 760                 765

Glu Gly Phe Met Lys Ala Ser Asp Gly Lys Thr Cys Leu Ala Leu Asp
    770                 775                 780

Gly His Gln Leu Leu Ala Gly Gly Glu Val Asp Leu Lys Asn Gln Val
785                 790                 795                 800

Thr Pro Leu Asp Ile Leu Ser Lys Thr Arg Val Ser Glu Asp Asn Ile
                805                 810                 815

Thr Glu Ser Gln His Met Leu Val Ala Glu Ile Met Val Ser Asp Gln
            820                 825                 830

Asp Asp Cys Ala Pro Val Gly Cys Ser Met Tyr Ala Arg Cys Ile Ser
```

```
                    835                 840                 845

Glu Gly Glu Asp Ala Thr Cys Gln Cys Leu Lys Gly Phe Ala Gly Asp
    850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
                885                 890                 895

Cys Arg Cys Ser Glu Gly Tyr Gln Gly Asp Gly Ile His Cys Leu Asp
            900                 905                 910

Ile Asp Glu Cys Gln Leu Gly Val His Ser Cys Gly Glu Asn Ala Ser
        915                 920                 925

Cys Thr Asn Thr Glu Gly Gly Tyr Thr Cys Met Cys Ala Gly Arg Leu
    930                 935                 940

Ser Glu Pro Gly Leu Ile Cys Pro Asp Ser Thr Pro Pro His Leu
945                 950                 955                 960

Arg Glu Asp Asp His His Tyr Ser Val Arg Asn Ser Asp Ser Glu Cys
                965                 970                 975

Pro Leu Ser His Asp Gly Tyr Cys Leu His Asp Gly Val Cys Met Tyr
            980                 985                 990

Ile Glu Ala Leu Asp Lys Tyr Ala Cys Asn Cys Val Val Gly Tyr Ile
        995                 1000                1005

Gly Glu Arg Cys Gln Tyr Arg Asp Leu Lys Trp Trp Glu Leu Arg His
    1010                1015                1020

Ala Gly His Gly Gln Gln Gln Lys Val Ile Val Val Ala Val Cys Val
1025                1030                1035                1040

Val Val Leu Val Met Leu Leu Leu Ser Leu Trp Gly Ala His Tyr
                1045                1050                1055

Tyr Arg Thr Gln Lys Leu Leu Ser Lys Asn Pro Lys Asn Pro Tyr Glu
            1060                1065                1070

Glu Ser Ser Arg Asp Val Arg Ser Arg Arg Pro Ala Asp Thr Glu Asp
        1075                1080                1085

Gly Met Ser Ser Cys Pro Gln Pro Trp Phe Val Val Ile Lys Glu His
    1090                1095                1100

Gln Asp Leu Lys Asn Gly Gly Gln Pro Val Ala Gly Glu Asp Gly Gln
1105                1110                1115                1120

Ala Ala Asp Gly Ser Met Gln Pro Thr Ser Trp Arg Gln Glu Pro Gln
                1125                1130                1135

Leu Cys Gly Met Gly Thr Glu Gln Gly Cys Trp Ile Pro Val Ser Ser
            1140                1145                1150

Asp Lys Gly Ser Cys Pro Gln Val Met Glu Arg Ser Phe His Met Pro
        1155                1160                1165

Ser Tyr Gly Thr Gln Thr Leu Glu Gly Gly Val Glu Lys Pro His Ser
    1170                1175                1180

Leu Leu Ser Ala Asn Pro Leu Trp Gln Gln Arg Ala Leu Asp Pro Pro
1185                1190                1195                1200

His Gln Met Glu Leu Thr Gln
                1205

<210> SEQ ID NO 3
<211> LENGTH: 160
<212> TYPE: PRT
<213> ORGANISM: Homo sapiens

<400> SEQUENCE: 3
```

```
Met Val Pro Ser Ala Gly Gln Leu Ala Leu Phe Ala Leu Gly Ile Val
 1               5                  10                  15

Leu Ala Ala Cys Gln Ala Leu Glu Asn Ser Thr Ser Pro Leu Ser Ala
                20                  25                  30

Asp Pro Val Ala Ala Val Val Ser His Phe Asn Asp Cys Pro
         35                  40                  45

Asp Ser His Thr Gln Phe Cys Phe His Gly Thr Cys Arg Phe Leu Val
        50                  55                  60

Gln Glu Asp Lys Pro Ala Cys Val Cys His Ser Gly Tyr Val Gly Ala
 65                  70                  75                  80

Arg Cys Glu His Ala Asp Leu Leu Ala Val Ala Ala Ser Gln Lys
                 85                  90                  95

Lys Gln Ala Ile Thr Ala Leu Val Val Val Ser Ile Val Ala Leu Ala
                100                 105                 110

Val Leu Ile Ile Thr Cys Val Leu Ile His Cys Cys Gln Val Arg Lys
            115                 120                 125

His Cys Glu Trp Cys Arg Ala Leu Ile Cys Arg His Glu Lys Pro Ser
    130                 135                 140

Ala Leu Leu Lys Gly Arg Thr Ala Cys Cys His Ser Glu Thr Val Val
145                 150                 155                 160

<210> SEQ ID NO 4
<211> LENGTH: 1255
<212> TYPE: PRT
<213> ORGANISM: Homo sapiens

<400> SEQUENCE: 4

Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
                100                 105                 110

Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220
```

-continued

```
Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
        260                 265                 270

Thr Tyr Asn Thr Asp Thr Phe Glu Ser Met Pro Asn Pro Glu Gly Arg
    275                 280                 285

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
        340                 345                 350

Val Arg Ala Val Thr Ser Ala Asn Ile Gln Glu Phe Ala Gly Cys Lys
    355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
            405                 410                 415

Asp Ser Leu Pro Asp Leu Ser Val Phe Gln Asn Leu Gln Val Ile Arg
        420                 425                 430

Gly Arg Ile Leu His Asn Gly Ala Tyr Ser Leu Thr Leu Gln Gly Leu
    435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
        500                 505                 510

Gln Leu Cys Ala Arg Gly His Cys Trp Gly Pro Gly Pro Thr Gln Cys
    515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
            565                 570                 575

Phe Gly Pro Glu Ala Asp Gln Cys Val Ala Cys Ala His Tyr Lys Asp
        580                 585                 590

Pro Pro Phe Cys Val Ala Arg Cys Pro Ser Gly Val Lys Pro Asp Leu
    595                 600                 605

Ser Tyr Met Pro Ile Trp Lys Phe Pro Asp Glu Glu Gly Ala Cys Gln
610                 615                 620

Pro Cys Pro Ile Asn Cys Thr His Ser Cys Val Asp Leu Asp Asp Lys
625                 630                 635                 640
```

-continued

```
Gly Cys Pro Ala Glu Gln Arg Ala Ser Pro Leu Thr Ser Ile Ile Ser
            645                 650                 655

Ala Val Val Gly Ile Leu Leu Val Val Leu Gly Val Val Phe Gly
            660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
            690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                    725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
            770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                    805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                    885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                    965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr Leu
            1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
                    1045                1050                1055

Gly Asp Leu Thr Leu Gly Leu Glu Pro Ser Glu Glu Glu Ala Pro Arg
```

-continued

```
                      1060                1065                1070
Ser Pro Leu Ala Pro Ser Glu Gly Ala Gly Ser Asp Val Phe Asp Gly
            1075                1080                1085
Asp Leu Gly Met Gly Ala Ala Lys Gly Leu Gln Ser Leu Pro Thr His
        1090                1095                1100
Asp Pro Ser Pro Leu Gln Arg Tyr Ser Glu Asp Pro Thr Val Pro Leu
1105                1110                1115                1120
Pro Ser Glu Thr Asp Gly Tyr Val Ala Pro Leu Thr Cys Ser Pro Gln
                1125                1130                1135
Pro Glu Tyr Val Asn Gln Pro Asp Val Arg Pro Gln Pro Pro Ser Pro
            1140                1145                1150
Arg Glu Gly Pro Leu Pro Ala Ala Arg Pro Ala Gly Ala Thr Leu Glu
        1155                1160                1165
Arg Pro Lys Thr Leu Ser Pro Gly Lys Asn Gly Val Val Lys Asp Val
    1170                1175                1180
Phe Ala Phe Gly Gly Ala Val Glu Asn Pro Glu Tyr Leu Thr Pro Gln
1185                1190                1195                1200
Gly Gly Ala Ala Pro Gln Pro His Pro Pro Pro Ala Phe Ser Pro Ala
                1205                1210                1215
Phe Asp Asn Leu Tyr Tyr Trp Asp Gln Asp Pro Pro Glu Arg Gly Ala
            1220                1225                1230
Pro Pro Ser Thr Phe Lys Gly Thr Pro Thr Ala Glu Asn Pro Glu Tyr
        1235                1240                1245
Leu Gly Leu Asp Val Pro Val
    1250                1255

<210> SEQ ID NO 5
<211> LENGTH: 1270
<212> TYPE: DNA
<213> ORGANISM: Homo sapiens

<400> SEQUENCE: 5
agacgttcgc acacctgggt gccagcgccc cagaggtccc gggacagccc gaggcgccgc     60
gcccgccgcc ccgagctccc caagccttcg agagcggcgc acactcccgg tctccactcg    120
ctcttccaac acccgctcgt tttggcggca gctcgtgtcc cagagaccga gttgccccag    180
agaccgagac gccgccgctg cgaaggacca atgagagccc gctgctaccg ccggcgccg     240
gtggtgctgt cgctcttgat actcggctca ggccattatg ctgctggatt ggacctcaat    300
gacacctact ctgggaagcg tgaaccattt tctgggacca cagtgctga tggatttgag     360
gttacctcaa gaagtgagat gtcttcaggg agtgagattt ccctgtgag tgaaatgcct     420
tctagtagtg aaccgtcctc gggagccgac tatgactact cagaagagta tgataacgaa    480
ccacaaatac ctgctatat tgtcgatgat tcagtcagag ttgaacaggt agttaagccc    540
ccccaaaaca agacggaaag tgaaaatact tcagataaac ccaaaagaaa gaaaagggga    600
ggcaaaaatg gaaaaaatag aagaacagaa gaagaaaa atccatgtaa tgcagaattt     660
caaaatttct gcattcacgg agaatgcaaa tatatagagc acctggaagc agtaacatgc    720
aaatgtcagc aagaatattt cggtgaacgg tgtgggaaa agtccatgaa actcacagc     780
atgattgaca gtagtttatc aaaaattgca ttagcagcca tagctgcctt tatgtctgct    840
gtgatcctca cagctgttgc tgttattaca gtccagctta aagacaata cgtcaggaaa    900
tatgaaggag aagctgagga acgaaagaaa cttcgacaag agaatggaaa tgtacatgct    960
atagcataac tgaagataaa attacaggat atcacattgg agtcactgcc aagtcatagc   1020
```

```
cataaatgat gagtcggtcc tctttccagt ggatcataag acaatggacc cttttttgtta    1080 tgatggtttt aaactttcaa ttgtcacttt ttatgctatt tctgtatata aaggtgcacg    1140
aaggtaaaaa gtatttttc aagttgtaaa taatttattt aatatttaat ggaagtgtat    1200
ttattttaca gctcattaaa cttttttaac caaacagaaa aaaaaaaaaa aaaaaaaaa    1260 aaaaaaaaaa                                                          1270

<210> SEQ ID NO 6
<211> LENGTH: 4877
<212> TYPE: DNA
<213> ORGANISM: Homo sapiens

<400> SEQUENCE: 6
actgttggga gaggaatcgt atctccatat ttcttctttc agccccaatc caagggttgt      60
agctggaact ttccatcagt tcttcctttc ttttcctct ctaagccttt gccttgctct     120
gtcacagtga agtcagccag agcagggctg ttaaactctg tgaaatttgt cataagggtg     180
tcaggtattt cttactggct tccaaagaaa catagataaa gaaatctttc ctgtggcttc     240
ccttggcagg ctgcattcag aaggtctctc agttgaagaa agagcttgga ggacaacagc     300
acaacaggag agtaaaagat gccccagggc tgaggcctcc gctcaggcag ccgcatctgg     360
ggtcaatcat actcaccttg cccgggccat gctccagcaa atcaagctg ttttcttttg     420 aaagttcaaa ctcatcaaga ttatgctgct cactcttatc attctgttgc cagtagtttc     480
aaaatttagt tttgttagtc tctcagcacc gcagcactgg agctgtcctg aaggtactct     540
cgcaggaaat gggaattcta cttgtgtggg tcctgcaccc ttcttaattt ctcccatgg      600 aaatagtatc tttaggattg acacagaagg aaccaattat gagcaattgg tggtggatgc     660
tggtgtctca gtgatcatgg attttcatta taatgagaaa agaatctatt gggtggattt     720
agaaagacaa cttttgcaaa gagttttct gaatgggtca aggcaagaga gagtatgtaa     780
tatagagaaa aatgtttctg gaatggcaat aaattggata aatgaagaag ttatttggtc     840
aaatcaacag gaaggaatca ttacagtaac agatatgaaa ggaaataatt cccacattct     900
tttaagtgct ttaaaatatc ctgcaaatgt agcagttgat ccagtagaaa ggtttatatt     960
ttggtcttca gaggtggctg gaagcctttt atagagcagat ctcgatggtg tgggagtgaa    1020
ggctctgttg gagacatcag agaaaataac agctgtgtca ttggatgtgc ttgataagcg    1080
gctgttttgg attcagtaca acagagaagg aagcaattct cttatttgct cctgtgatta    1140
tgatggaggt tctgtccaca ttagtaaaca tccaacacag cataatttgt ttgcaatgtc    1200 ccttttttggt gaccgtatct tctattcaac atggaaaatg aagacaattt ggatagccaa    1260
caaacacact ggaaaggaca tggttagaat taacctccat tcatcatttg taccacttgg    1320
tgaactgaaa gtagtgcatc cacttgcaca acccaaggca gaagatgaca cttgggagcc    1380
tgagcagaaa cttttgcaaat tgaggaaagg aaactgcagc agcactgtgt gtgggcaaga    1440
cctccagtca cacttgtgca tgtgtgcaga gggatacgcc ctaagtcgag accggaagta    1500
ctgtgaagat gttaatgaat gtgcttttg gaatcatggc tgtactcttg ggtgtaaaaa    1560
cacccctgga tcctattact gcacgtgccc tgtaggattt gttctgcttc ctgatgggaa    1620
acgatgtcat caacttgttt cctgtccacg caatgtgtct gaatgcagcc atgactgtgt    1680
tctgacatca gaaggtccct tatgttttctg tcctgaaggc tcagtgcttg agagagatgg    1740
gaaaacatgt agcggttgtt cctcacccga taatggtgga tgtagccagc tctgcgttcc    1800
```

```
tcttagccca gtatcctggg aatgtgattg cttttcctggg tatgacctac aactggatga    1860
aaaaagctgt gcagcttcag gaccacaacc attttttgctg tttgccaatt ctcaagatat    1920
tcgacacatg cattttgatg aacagacta tggaactctg ctcagccagc agatgggaat     1980
ggtttatgcc ctagatcatg accctgtgga aaataagata tactttgccc atacagccct    2040
gaagtggata gagagagcta atatggatgt tcccagcga gaaaggctta ttgaggaagg     2100
agtagatgtg ccagaaggtc ttgctgtgga ctggattggc cgtagattct attggacaga    2160
cagagggaaa tctctgattg aaggagtga tttaaatggg aaacgttcca aaataatcac     2220
taaggagaac atctctcaac cacgaggaat tgctgttcat ccaatggcca agagattatt    2280
ctggactgat acaggatta atccacgaat tgaaagttct tccctccaag gccttggccg     2340
tctggttata gccagctctg atctaatctg gccagtgga ataacgattg acttcttaac     2400
tgacaagttg tactggtgcg atgccaagca gtctgtgatt gaaatggcca atctggatgg    2460
ttcaaaacgc cgaagactta cccagaatga tgtaggtcac ccatttgctg tagcagtgtt    2520
tgaggattat gtgtggttct cagattgggc tatgccatca gtaataagag taaacaagag    2580
gactggcaaa gatagagtac gtctccaagg cagcatgctg aagccctcat cactggttgt    2640
ggttcatcca ttggcaaaac caggagcaga tccctgctta tatcaaaacg gaggctgtga    2700
acatatttgc aaaagaggc ttggaactgc ttggtgttcg tgtcgtgaag gttttatgaa     2760
agcctcagat gggaaaacgt gtctggctct ggatggtcat cagctgttgg caggtggtga    2820
agttgatcta aagaaccaag taacaccatt ggacatcttg tccaagacta gagtgtcaga    2880
agataacatt acagaatctc aacacatgct agtggctgaa atcatggtgt cagatcaaga    2940
tgactgtgct cctgtgggat gcagcatgta tgctcggtgt atttcagagg gagaggatgc    3000
cacatgtcag tgtttgaaag gatttgctgg ggatggaaaa ctatgttctg atatagatga    3060
atgtgagatg ggtgtcccag tgtgccccc tgcctcctcc aagtgcatca acaccgaagg    3120
tggttatgtc tgccggtgct cagaaggcta ccaaggagat gggattcact gtcttgatat    3180
tgatgagtgc caactggggg tgcacagctg tggagagaat gccagctgca caaatacaga    3240
gggaggctat acctgcatgt gtgctggacg cctgtctgaa ccaggactga tttgccctga    3300
ctctactcca ccccctcacc tcagggaaga tgaccaccac tattccgtaa gaaatagtga    3360
ctctgaatgt ccctgtccc acgatgggta ctgcctccat gatggtgtgt gcatgtatat    3420
tgaagcattg gacaagtatg catgcaactg tgttgttggc tacatcgggg agcgatgtca    3480
gtaccgagac ctgaagtggt gggaactgcg ccacgctggc cacgggcagc agcagaaggt    3540
catcgtggtg gctgtctgcg tggtggtgct tgtcatgctg ctcctcctga gcctgtgggg    3600
ggcccactac tacaggactc agaagctgct atcgaaaaac ccaaagaatc cttatgagga    3660
gtcgagcaga gatgtgagga gtcgcaggcc tgctgacact gaggatggga tgtcctcttg    3720
ccctcaacct tggtttgtgg ttataaaaga acaccaagac ctcaagaatg ggggtcaacc    3780
agtggctggt gaggatggcc aggcagcaga tgggtcaatg caaccaactt catggaggca    3840
ggagccccag ttatgtggaa tgggcacaga gcaaggctgc tggattccag tatccagtga    3900
taagggctcc tgtcccagg taatggagcg aagctttcat atgccctcct atgggacaca    3960
gacccttgaa gggggtgtcg agaagcccca ttctctccta tcagctaacc cattatggca    4020
acaaagggcc ctggacccac acaccaaat ggagctgact cagtgaaaac tggaattaaa     4080
aggaaagtca agaagaatga actatgtcga tgcacagtat cttttctttc aaaagtagag    4140
caaaactata ggttttggtt ccacaatctc tacgactaat cacctactca atgcctggag    4200
```

| | |
|---|---|
| acagatacgt agttgtgctt ttgtttgctc ttttaagcag tctcactgca gtcttatttc | 4260 |
| caagtaagag tactgggaga atcactaggt aacttattag aaacccaaat tgggacaaca | 4320 |
| gtgctttgta aattgtgttg tcttcagcag tcaatacaaa tagattttg tttttgttgt | 4380 |
| tcctgcagcc ccagaagaaa ttaggggtta agcagacag tcacactggt ttggtcagtt | 4440 |
| acaaagtaat ttcttttgatc tggacagaac atttatatca gtttcatgaa atgattggaa | 4500 |
| tattacaata ccgttaagat acagtgtagg catttaactc ctcattggcg tggtccatgc | 4560 |
| tgatgatttt gccaaaatga gttgtgatga atcaatgaaa aatgtaattt agaaactgat | 4620 |
| ttcttcagaa ttagatggcc ttatttttta aaatatttga atgaaaacat tttatttta | 4680 |
| aaatattaca caggaggcct tcggagtttc ttagtcatta ctgtccttt ccctacaga | 4740 |
| attttccctc ttggtgtgat tgcacagaat ttgtatgtat tttcagttac aagattgtaa | 4800 |
| gtaaattgcc tgatttgttt tcattataga caacgatgaa tttcttctaa ttatttaaat | 4860 |
| aaaatcacca aaaacat | 4877 |

<210> SEQ ID NO 7
<211> LENGTH: 4119
<212> TYPE: DNA
<213> ORGANISM: Homo sapiens

<400> SEQUENCE: 7

| | |
|---|---|
| ctggagagcc tgctgcccgc ccgcccgtaa aatggtcccc tcggctggac agctcgccct | 60 |
| gttcgctctg ggtattgtgt tggctgcgtg ccaggccttg gagaacagca cgtccccgct | 120 |
| gagtgcagac ccgcccgtgg ctgcagcagt ggtgtcccat tttaatgact gcccagattc | 180 |
| ccacactcag ttctgcttcc atggaacctg caggtttttg gtgcaggagg acaagccagc | 240 |
| atgtgtctgc cattctgggt acgttggtgc acgctgtgag catgcggacc tcctggccgt | 300 |
| ggtggctgcc agccagaaga agcaggccat caccgccttg gtggtggtct ccatcgtggc | 360 |
| cctggctgtc cttatcatca catgtgtgct gatacactgc tgccaggtcc gaaaacactg | 420 |
| tgagtggtgc cgggcccctca tctgccggca cgagaagccc agcgccctcc tgaagggaag | 480 |
| aaccgcttgc tgccactcag aaacagtggt ctgaagagcc cagaggagga gtttggccag | 540 |
| gtggactgtg gcagatcaat aaagaaaggc ttcttcagga cagcactgcc agagatgcct | 600 |
| gggtgtgcca cagaccttcc tacttggcct gtaatcacct gtgcagcctt ttgtgggcct | 660 |
| tcaaaactct gtcaagaact ccgtctgctt ggggttattc agtgtgacct agagaagaaa | 720 |
| tcagcggacc acgatttcaa gacttgttaa aaaagaactg caaagagacg gactcctgtt | 780 |
| cacctaggtg aggtgtgtgc agcagttggt gtctgagtcc acatgtgtgc agttgtcttc | 840 |
| tgccagccat ggattccagg ctatatattt cttttttaatg ggccacctcc ccacaacaga | 900 |
| attctgccca acacaggaga tttctatagt tattgttttc tgtcatttgc ctactgggga | 960 |
| agaaagtgaa ggaggggaaa ctgtttaata tcacatgaag accctagctt taagagaagc | 1020 |
| tgtatcctct aaccacgaga ctctcaacca gcccaacatc ttccatggac acatgacatt | 1080 |
| gaagaccatc ccaagctatc gccacccttg agatgatgt cttatttatt agatggataa | 1140 |
| tggtttattt tttaatctct taagtcaatg taaaaagtat aaaaccccctt cagacttcta | 1200 |
| cattaatgat gtatgtgttg ctgactgaaa agctatactg attagaaatg tctggcctct | 1260 |
| tcaagacagc taaggcttgg gaaaagtctt ccagggtgcg gagatggaac cagaggctgg | 1320 |
| gttactggta ggaataaagg tagggggttca gaaatggtgc cattgaagcc acaaagccgg | 1380 |

```
taaatgcctc aatacgttct gggagaaaac ttagcaaatc catcagcagg gatctgtccc    1440
ctctgttggg gagagaggaa gagtgtgtgt gtctacacag gataaaccca atacatattg    1500
tactgctcag tgattaaatg ggttcacttc ctcgtgagcc ctcggtaagt atgtttagaa    1560
atagaacatt agccacgagc cataggcatt tcaggccaaa tccatgaaag ggggaccagt    1620 cattttatttt ccattttgtt gcttggttgg tttgttgctt tatttttaaa aggagaagtt    1680
taactttgct atttattttc gagcactagg aaaactattc cagtaatttt tttttcctca    1740
tttccattca ggatgccggc tttattaaca aaaactctaa caagtcacct ccactatgtg    1800
ggtcttcctt tcccctcaag agaaggagca attgttcccc tgacatctgg gtccatctga    1860
cccatggggc ctgcctgtga gaaacagtgg gtcccttcaa atacatagtg gatagctcat    1920
ccctaggaat tttcattaaa atttggaaac agagtaatga agaataata tataaactcc    1980 ttatgtgagg aaatgctact aatatctgaa aagtgaaaga tttctatgta ttaactctta    2040
agtgcaccta gctattaca tcgtgaaagg tacatttaaa atatgttaaa ttggcttgaa    2100
attttcagag aattttgtct tcccctaatt cttcttcctt ggtctggaag aacaatttct    2160
atgaattttc tctttatttt tttttttataa ttcagacaat tctatgaccc gtgtcttcat    2220
ttttggcact cttatttaac aatgccacac ctgaagcact tggatctgtt cagagctgac    2280
cccctagcaa cgtagttgac acagctccag gttttttaaat tactaaaata agttcaagtt    2340
tacatccctt gggccagata tgtgggttga ggcttgactg tagcatcctg cttagagacc    2400
aatcaatgga cactggtttt tagacctcta tcaatcagta gttagcatcc aagagacttt    2460
gcagaggcgt aggaatgagg ctggacagat ggcggaacga gaggttccct gcgaagactt    2520
gagatttagt gtctgtgaat gttctagttc ctaggtccag caagtcacac ctgccagtgc    2580
cctcatcctt atgcctgtaa cacacatgca gtgagaggcc tcacatatac gcctccctag    2640
aagtgccttc caagtcagtc ctttggaaac cagcaggtct gaaaagagg ctgcatcaat    2700 gcaagcctgg ttggaccatt gtccatgcct caggatagaa cagcctggct tatttgggga    2760
tttttcttct agaaatcaaa tgactgataa gcattggctc cctctgccat ttaatgcaa    2820 tggtagtctt tggttagctg caaaaatact ccatttcaag ttaaaaatgc atcttctaat    2880
ccatctctgc aagctccctg tgtttccttg cccttagaa aatgaattgt tcactacaat    2940
tagagaatca tttaacatcc tgacctggta agctgccaca cacctggcag tggggagcat    3000
cgctgtttcc aatggctcag gagacaatga aaagccccca tttaaaaaaa taacaaacat    3060 ttttttaaaag gcctccaata ctcttatgga gcctggattt ttcccactgc tctacaggct    3120
gtgacttttt ttaagcatcc tgacaggaaa tgttttcttc tacatggaaa gatagacagc    3180
agccaaccct gatctggaag acagggcccc ggctggacac acgtgaacc aagccaggga    3240 tgggctggcc attgtgtccc cgcaggagag atgggcagaa tggccctaga gttcttttcc    3300
ctgagaaagg agaaaaagat gggattgcca ctcacccacc cacactggta agggaggaga    3360
atttgtgctt ctggagcttc tcaagggatt gtgttttgca ggtacagaaa actgcctgtt    3420
atcttcaagc caggttttcg agggcacatg ggtcaccagt tgcttttca gtcaatttgg    3480 ccgggatgga ctaatgaggc tctaacactg ctcaggagac ccctgccctc tagttggttc    3540
tgggctttga tctcttccaa cctgcccagt cacagaagga ggaatgactc aaatgcccaa    3600
aaccaagaac acattgcaga agtaagacaa acatgtatat ttttaaatgt tctaacataa    3660
gacctgttct ctctagccat tgatttacca ggctttctga aagatctagt ggttcacaca    3720
gagagagaga gagtactgaa aaagcaactc ctccttcttag tcttaataat ttactaaaat    3780
```

| | | | | |
|---|---|---|---|---|
| ggtcaacttt | tcattatctt | tattataata | aacctgatgc | ttttttttag aactccttac | 3840 |
| tctgatgtct | gtatatgttg | cactgaaaag | gttaatattt | aatgttttaa tttatttttgt | 3900 |
| gtggtaagtt | aattttgatt | tctgtaatgt | gttaatgtga | ttagcagtta ttttccttaa | 3960 |
| tatctgaatt | atacttaaag | agtagtgagc | aatataagac | gcaattgtgt ttttcagtaa | 4020 |
| tgtgcattgt | tattgagttg | tactgtacct | tatttggaag | gatgaaggaa tgaacctttt | 4080 |
| tttcctaaaa | aaaaaaaaaa | aaaaaaaaaa | aaaaaaaa | | 4119 |

```
<210> SEQ ID NO 8
<211> LENGTH: 4624
<212> TYPE: DNA
<213> ORGANISM: Homo sapiens

<400> SEQUENCE: 8
```

| | | | | |
|---|---|---|---|---|
| ggaggaggtg | gaggaggagg | gctgcttgag | gaagtataag | aatgaagttg tgaagctgag | 60 |
| attcccctcc | attgggaccg | gagaaaccag | gggagccccc | cgggcagccg cgcgcccctt | 120 |
| cccacgggc | cctttactgc | gccgcgcgcc | cggcccccac | ccctcgcagc accccgcgcc | 180 |
| ccgcgccctc | ccagccgggt | ccagccggag | ccatggggcc | ggagccgcag tgagcaccat | 240 |
| ggagctggcg | gccttgtgcc | gctggggggct | cctcctcgcc | ctcttgcccc cggagccgc | 300 |
| gagcacccaa | gtgtgcaccg | gcacagacat | gaagctgcgg | ctccctgcca gtcccgagac | 360 |
| ccacctggac | atgctccgcc | acctctacca | gggctgccag | gtggtgcagg gaaacctgga | 420 |
| actcacctac | ctgcccacca | atgccagcct | gtccttcctg | caggatatcc aggaggtgca | 480 |
| gggctacgtg | ctcatcgctc | acaaccaagt | gaggcaggtc | ccactgcaga ggctgcggat | 540 |
| tgtgcgaggc | acccagctct | ttgaggacaa | ctatgccctg | gccgtgctag acaatggaga | 600 |
| cccgctgaac | aataccaccc | ctgtcacagg | ggcctcccca | ggaggcctgc gggagctgca | 660 |
| gcttcgaagc | ctcacagaga | tcttgaaagg | aggggtcttg | atccagcgga accccccagct | 720 |
| ctgctaccag | gacacgattt | tgtggaagga | catcttccac | aagaacaacc agctggctct | 780 |
| cacactgata | gacaccaacc | gctctcgggc | ctgccaccc | tgttctccga tgtgtaaggg | 840 |
| ctcccgctgc | tggggagaga | gttctgagga | ttgtcagagc | ctgacgcgca ctgtctgtgc | 900 |
| cggtggctgt | gcccgctgca | aggggccact | gcccactgac | tgctgccatg agcagtgtgc | 960 |
| tgccggctgc | acgggcccca | agcactctga | ctgcctggcc | tgcctccact tcaaccacag | 1020 |
| tggcatctgt | gagctgcact | gcccagccct | ggtcacctac | aacacagaca cgtttgagtc | 1080 |
| catgcccaat | cccgagggcc | ggtatacatt | cggcgccagc | tgtgtgactg cctgtccta | 1140 |
| caactaccctt | tctacggacg | tgggatcctg | caccctcgtc | tgccccctgc acaaccaaga | 1200 |
| ggtgacagca | gaggatggaa | cacagcggtg | tgagaagtgc | agcaagccct gtgcccgagt | 1260 |
| gtgctatggt | ctgggcatgg | agcacttgcg | agaggtgagg | gcagttacca gtgccaatat | 1320 |
| ccaggagttt | gctggctgca | agaagatctt | tgggagcctg | gcatttctgc cggagagctt | 1380 |
| tgatggggac | ccagcctcca | acactgcccc | gctccagcca | gagcagctcc aagtgtttga | 1440 |
| gactctggaa | gagatcacag | gttacctata | catctcagca | tggccggaca gcctgcctga | 1500 |
| cctcagcgtc | ttccagaacc | tgcaagtaat | ccggggacga | attctgcaca atggcgccta | 1560 |
| ctcgctgacc | ctgcaagggc | tgggcatcag | ctggctgggg | ctgcgctcac tgagggaact | 1620 |
| gggcagtgga | ctggccctca | tccaccataa | cacccacctc | tgcttcgtgc acacggtgcc | 1680 |
| ctgggaccag | ctctttcgga | acccgcacca | agctctgctc | cacactgcca accggccaga | 1740 |

```
ggacgagtgt gtgggcgagg gcctggcctg ccaccagctg tgcgcccgag ggcactgctg    1800
gggtccaggg cccacccagt gtgtcaactg cagccagttc cttcggggcc aggagtgcgt    1860
ggaggaatgc cgagtactgc aggggctccc cagggagtat gtgaatgcca ggcactgttt    1920
gccgtgccac cctgagtgtc agcccagaa tggctcagtg acctgttttg gaccggaggc     1980
tgaccagtgt gtggcctgtg cccactataa ggaccctccc ttctgcgtgg cccgctgccc    2040
cagcggtgtg aaacctgacc tctcctacat gcccatctgg aagtttccag atgaggaggg    2100
cgcatgccag ccttgcccca tcaactgcac ccactcctgt gtggacctgg atgacaaggg    2160
ctgccccgcc gagcagagag ccagccctct gacgtccatc atctctgcgg tggttggcat    2220
tctgctggtc gtggtcttgg gggtggtctt tgggatcctc atcaagcgac ggcagcagaa    2280
gatccggaag tacacgatgc ggagactgct gcaggaaacg gagctggtgg agccgctgac    2340
acctagcgga gcgatgccca accaggcgca gatgcggatc ctgaaagaga cggagctgag    2400
gaaggtgaag gtgcttggat ctggcgcttt tggcacagtc tacaagggca tctggatccc    2460
tgatggggag aatgtgaaaa ttccagtggc catcaaagtg ttgagggaaa acacatcccc    2520
caaagccaac aaagaaatct agacgaagca tacgtgatgc tggtgtgg ctccccata      2580 tgtctcccgc cttctgggca tctgcctgac atccacggtg cagctggtga cacagcttat    2640
gccctatggc tgcctcttag accatgtccg ggaaaaccgc ggacgcctgg gctcccagga    2700
cctgctgaac tggtgtatgc agattgccaa ggggatgagc tacctggagg atgtgcggct    2760
cgtacacagg gacttggccg ctcggaacgt gctggtcaag agtcccaacc atgtcaaaat    2820
tacagacttc gggctggctc ggctgctgga cattgacgag acagagtacc atgcagatgg    2880
gggcaaggtg cccatcaagt ggatggcgct ggagtccatt ctccgccggc ggttcaccca    2940
ccagagtgat gtgtggagtt atggtgtgac tgtgtgggag ctgatgactt ttggggccaa    3000
accttacgat gggatcccag cccgggagat ccctgacctg ctggaaaagg gggagcggct    3060
gccccagccc cccatctgca ccattgatgt ctacatgatc atggtcaaat gttggatgat    3120
tgactctgaa tgtcggccaa gattccggga gttggtgtct gaattctccc gcatggccag    3180 ggaccccag cgctttgtgg tcatccagaa tgaggacttg ggcccagcca gtcccttgga    3240
cagcaccttc taccgctcac tgctggagga cgatgacatg ggggacctgg tggatgctga    3300
ggagtatctg gtaccccagc agggcttctt ctgtccagac cctgccccgg cgctggggg     3360 catggtccac cacaggcacc gcagctcatc taccaggagt ggcggtgggg acctgacact    3420
agggctggag ccctctgaag aggaggcccc caggtctcca ctggcaccct ccgaaggggc    3480
tggctccgat gtatttgatg gtgacctggg aatgggggca gccaagggc tgcaaagcct     3540 ccccacacat gaccccagcc ctctacagcg gtacagtgag gaccccacag tacccctgcc    3600
ctctgagact gatggctacg ttgcccccct gacctgcagc cccagcctg aatatgtgaa     3660 ccagccagat gttcggcccc agccccttc gccccgagag ggcctctgc ctgctgcccg      3720 acctgctggt gccactctgg aaaggcccaa gactctctcc caggaaga atggggtcgt      3780 caaagacgtt tttgcctttg gggtgccgt ggagaacccc gagtacttga cccccaggg      3840 aggagctgcc cctcagcccc acctcctcc tgccttcagc ccagccttcg acaacctcta    3900
ttactgggac caggacccac cagagcgggg ggctccaccc agcaccttca agggacacac    3960
tacggcagag aacccagagt acctgggtct ggacgtgcca gtgtgaacca gaaggccaag    4020
tccgcagaag ccctgatgtg tcctcaggga gcagggaagg cctgacttct gctggcatca    4080
agaggtggga gggccctccg accacttcca ggggaacctg ccatgccagg aacctgtcct    4140
```

```
aaggaacctt ccttcctgct tgagttccca gatggctgga aggggtccag cctcgttgga    4200
agaggaacag cactggggag tctttgtgga ttctgaggcc ctgcccaatg agactctagg    4260
gtccagtgga tgccacagcc cagcttggcc ctttccttcc agatcctggg tactgaaagc    4320
cttagggaag ctggcctgag aggggaagcg ccctaaggg agtgtctaag aacaaaagcg    4380
acccattcag agactgtccc tgaaacctag tactgccccc catgaggaag gaacagcaat    4440
ggtgtcagta tccaggcttt gtacagagtg ctttctgtt tagttttttac tttttttgtt    4500 ttgtttttttt aaagatgaaa taaagaccca gggggagaat gggtgttgta tgggaggca    4560 agtgtggggg gtccttctcc acacccactt tgtccatttg caaatatatt ttggaaaaca    4620
gcta                                                                4624

<210> SEQ ID NO 9
<211> LENGTH: 183
<212> TYPE: PRT
<213> ORGANISM: Homo sapiens

<400> SEQUENCE: 9

Met Arg Ala Asn Asp Ala Leu Gln Val Leu Gly Leu Leu Phe Ser Leu
  1               5                  10                  15

Ala Arg Gly Ser Glu Val Gly Asn Ser Gln Ala Val Cys Pro Gly Thr
                 20                  25                  30

Leu Asn Gly Leu Ser Val Thr Gly Asp Ala Glu Asn Gln Tyr Gln Thr
             35                  40                  45

Leu Tyr Lys Leu Tyr Glu Arg Cys Glu Val Val Met Gly Asn Leu Glu
         50                  55                  60

Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
                 85                  90                  95

Leu Pro Leu Pro Asn Leu Arg Val Val Arg Gly Thr Gln Val Tyr Asp
                100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Gly Gln Phe Pro
        130                 135                 140

Met Val Pro Ser Gly Leu Thr Pro Gln Pro Ala Gln Asp Trp Tyr Leu
145                 150                 155                 160

Leu Asp Asp Asp Pro Arg Leu Leu Thr Leu Ser Ala Ser Ser Lys Val
                165                 170                 175

Pro Val Thr Leu Ala Ala Val
            180

<210> SEQ ID NO 10
<211> LENGTH: 1050
<212> TYPE: DNA
<213> ORGANISM: Homo sapiens

<400> SEQUENCE: 10
acacacacac accctccccc tgccatccct ccccggactc cggctccggc tccgattgca      60
atttgcaacc tccgctgccg tcgccgcagc agccaccaat tcgccagcgg ttcaggtggc     120
tcttgcctcg atgtcctagc ctaggggccc ccgggccgga cttggctggg ctcccttcac     180
cctctgcgga gtcatgaggg cgaacgacgc tctgcaggtg ctgggcttgc ttttcagcct     240
```

```
ggcccggggc tccgaggtgg gcaactctca ggcagtgtgt cctgggactc tgaatggcct    300
gagtgtgacc ggcgatgctg agaaccaata ccagacactg tacaagctct acgagaggtg    360
tgaggtggtg atggggaacc ttgagattgt gctcacggga cacaatgccg acctctcctt    420
cctgcagtgg attcgagaag tgacaggcta tgtcctcgtg ccatgaatga aattctctac    480
tctaccattg cccaacctcc gcgtggtgcg agggacccag gtctacgatg ggaagtttgc    540
catcttcgtc atgttgaact ataacaccaa ctccagccac gctctgcgcc agctccgctt    600
gactcagctc accggtcagt tcccgatggt tccttctggc ctcacccctc agccagccca    660
agactggtac ctccttgatg atgacccaag actgctcact ctaagtgcct cttccaaggt    720
gcctgtcacc ttggccgctg tctaaaggtc cattgctccc taagcaatag agggccccca    780
gtaggggag ctaggggcat ctgctccagg gaaaggaacc ctgtgtcctt gtggggctgg    840
agtcagagct ggatctgtta accgtttttc taatttcaaa gtacagtgta ccggaggcca    900
ggcctgatgc cttacacctg taatcccagc attttgggag ccaaggagg gcagatcact    960
tgagatcagg agtttgagac cagcctggcc aacatggcga aaccctgtct ctactaaaaa    1020
tacaaaaaaa taaataaaa taaaaaatta                                       1050

<210> SEQ ID NO 11
<211> LENGTH: 1210
<212> TYPE: PRT
<213> ORGANISM: Homo sapiens

<400> SEQUENCE: 11

Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
```

-continued

```
                225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
        275                 280                 285
Ala Thr Cys Val Lys Lys Cys Pro Arg Asn Tyr Val Val Thr Asp His
    290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
                340                 345                 350
Ala Thr Asn Ile Lys His Phe Lys Asn Cys Thr Ser Ile Ser Gly Asp
            355                 360                 365
Leu His Ile Leu Pro Val Ala Phe Arg Gly Asp Ser Phe Thr His Thr
        370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
                420                 425                 430
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
        450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
        530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
```

-continued

```
Leu Leu Val Val Ala Leu Gly Ile Gly Leu Phe Met Arg Arg His
            660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
            690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                    725                 730                 735

Lys Val Lys Ile Pro Val Ala Ile Lys Glu Leu Arg Glu Ala Thr Ser
                    740                 745                 750

Pro Lys Ala Asn Lys Glu Ile Leu Asp Glu Ala Tyr Val Met Ala Ser
                    755                 760                 765

Val Asp Asn Pro His Val Cys Arg Leu Leu Gly Ile Cys Leu Thr Ser
            770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                    805                 810                 815

Trp Cys Val Gln Ile Ala Lys Gly Met Asn Tyr Leu Glu Asp Arg Arg
                    820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
            850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                    885                 890                 895

Val Trp Ser Tyr Gly Val Thr Val Trp Glu Leu Met Thr Phe Gly Ser
                    900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
            930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                    965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe Phe
    1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
                1045                1050                1055

Ser Cys Pro Ile Lys Glu Asp Ser Phe Leu Gln Arg Tyr Ser Ser Asp
        1060                1065                1070
```

```
Pro Thr Gly Ala Leu Thr Glu Asp Ser Ile Asp Asp Thr Phe Leu Pro
    1075                1080                1085

Val Pro Glu Tyr Ile Asn Gln Ser Val Pro Lys Arg Pro Ala Gly Ser
    1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
            1125                1130                1135

Glu Tyr Leu Asn Thr Val Gln Pro Thr Cys Val Asn Ser Thr Phe Asp
            1140                1145                1150

Ser Pro Ala His Trp Ala Gln Lys Gly Ser His Gln Ile Ser Leu Asp
            1155                1160                1165

Asn Pro Asp Tyr Gln Gln Asp Phe Phe Pro Lys Glu Ala Lys Pro Asn
    1170                1175                1180

Gly Ile Phe Lys Gly Ser Thr Ala Glu Asn Ala Glu Tyr Leu Arg Val
    1185                1190                1195                1200

Ala Pro Gln Ser Ser Glu Phe Ile Gly Ala
            1205                1210

<210> SEQ ID NO 12
<211> LENGTH: 628
<212> TYPE: PRT
<213> ORGANISM: Homo sapiens

<400> SEQUENCE: 12

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240
```

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
                355                 360                 365

Leu His Ile Leu Pro Val Ala Phe Arg Gly Asp Ser Phe Thr His Thr
            370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
            450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
            530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
            610                 615                 620

Thr Tyr Gly Ser
625

<210> SEQ ID NO 13
<211> LENGTH: 405

```
<212> TYPE: PRT
<213> ORGANISM: Homo sapiens

<400> SEQUENCE: 13

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400
```

```
Ile Thr Gly Leu Ser
            405
```

<210> SEQ ID NO 14
<211> LENGTH: 705
<212> TYPE: PRT
<213> ORGANISM: Homo sapiens

<400> SEQUENCE: 14

```
Met Arg Pro Ser Gly Thr Ala Gly Ala Ala Leu Leu Ala Leu Leu Ala
  1               5                  10                  15

Ala Leu Cys Pro Ala Ser Arg Ala Leu Glu Glu Lys Lys Val Cys Gln
             20                  25                  30

Gly Thr Ser Asn Lys Leu Thr Gln Leu Gly Thr Phe Glu Asp His Phe
         35                  40                  45

Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
```

-continued

```
            355                 360                 365
Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
        420                 425                 430

His Gly Gln Phe Ser Leu Ala Val Val Ser Leu Asn Ile Thr Ser Leu
                435                 440                 445

Gly Leu Arg Ser Leu Lys Glu Ile Ser Asp Gly Asp Val Ile Ile Ser
        450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
        500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
        530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
        610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
                645                 650                 655

Gln Ser Gly Ser Pro Ala Ala Gln Glu Ser Cys Leu Gly Trp Ile Pro
                660                 665                 670

Ser Leu Leu Pro Ser Glu Phe Gln Leu Gly Trp Gly Cys Ser His
        675                 680                 685

Leu His Ala Trp Pro Ser Ala Ser Val Ile Ile Thr Ala Ser Ser Cys
        690                 695                 700

His
705
```